US009198965B2

(12) United States Patent
Schultz-Cherry et al.

(10) Patent No.: US 9,198,965 B2
(45) Date of Patent: Dec. 1, 2015

(54) PEPTIDE ADJUVANT FOR INFLUENZA VACCINATION

(75) Inventors: Stacey L. Schultz-Cherry, Germantown, TN (US); Curtis R. Brandt, Stoughton, WI (US); Jeremy C. Jones, Memphis, TN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1447 days.

(21) Appl. No.: 12/484,831

(22) Filed: Jun. 15, 2009

(65) Prior Publication Data

US 2010/0040642 A1    Feb. 18, 2010

Related U.S. Application Data

(60) Provisional application No. 61/061,499, filed on Jun. 13, 2008.

(51) Int. Cl.
| | | |
|---|---|---|
| *A61K 38/00* | (2006.01) | |
| *A61K 39/145* | (2006.01) | |
| *A61K 39/00* | (2006.01) | |

(52) U.S. Cl.
CPC ........ *A61K 39/145* (2013.01); *A61K 2039/5252* (2013.01); *A61K 2039/55505* (2013.01); *A61K 2039/55516* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 5,624,898 A | 4/1997 | Frey, II | |
| 6,180,603 B1 | 1/2001 | Frey, II | |
| 6,313,093 B1 | 11/2001 | Frey, II | |
| 2003/0077289 A1 | 4/2003 | Wang | |
| 2005/0130884 A1* | 6/2005 | Brandt et al. | ............ 514/12 |
| 2005/0203024 A1 | 9/2005 | Brandt et al. | |
| 2007/0275014 A1* | 11/2007 | Yusibov et al. | ......... 424/209.1 |

FOREIGN PATENT DOCUMENTS

| | | |
|---|---|---|
| WO | 0033813 A1 | 6/2000 |
| WO | 0141782 A2 | 6/2001 |
| WO | 2005060541 A2 | 7/2005 |

OTHER PUBLICATIONS

Jones, et al., Inhibition of Influenza Virus Infection by a Novel Antiviral Peptide That Targets Viral Attachment to Cells, Journal of Virology, (2006) vol. 80(24), p. 11960-11967.
Schroeder and Lubke, in "The Peptides", vol. 1, Academic Press, New York, N.Y., pp. 2-136 (1965).
Johansson, et al., Journal of Virology, 1989, vol. 63(3), p. 1239-1246.
Cianci, et al., Journal of Virology, 73(3):1785-94 (1999).
Wild et al., Proc. Natl. Acad. Sci. USA, 89: 10537-10541 (1992).
Rimsky et al., J Virol, 72: 986-993 (1998).
Reed and Muench, Am. J. Hyg., vol. 27, pp. 493-497 (1938).
Lu, et al., "Immunity to influenza A H9N2 viruses induced by infection and vaccination," J. Virol., 2001, vol. 75(10), p. 4896-4901.
Katz, et al., "Adjuvant activity of the heat-labile enterotoxin from enterotoxigenic Escherichia coli for oral administration of inactivated influenza virus vaccine," J. Infect. Dis., 1997, vol. 175(2), p. 352-363.
Rowe, et al., "Detection of antibody to avian influenza a (H5N1) virus in human serum by using a combination of serologic assays," J. Clin. Microbiol., 1999, vol. 37(4), p. 937-943.
International Search Report and Written Opinion from PCT/US09/47411, dated Oct. 8, 2009.
International Search Report and Written Opinion from PCT/US09/47412, dated Dec. 15, 2009.
Supplementary European Search Report issued in European Patent Application No. 09763805.0 (2307036) dated Jul. 27, 2012.

* cited by examiner

*Primary Examiner* — Stacy B Chen
(74) *Attorney, Agent, or Firm* — Armstrong Teasdale LLP

(57) ABSTRACT

The present disclosure generally relates to peptides having adjuvant properties, vaccines comprising the adjuvant peptides, and their use in prophylaxis or therapy for influenza. More particularly, the invention relates to adjuvant peptides that induce aggregation of influenza virus. The peptides can be included in influenza vaccines to increase the immune response to the vaccine.

20 Claims, 20 Drawing Sheets

FIG. 2A
FIG. 2B
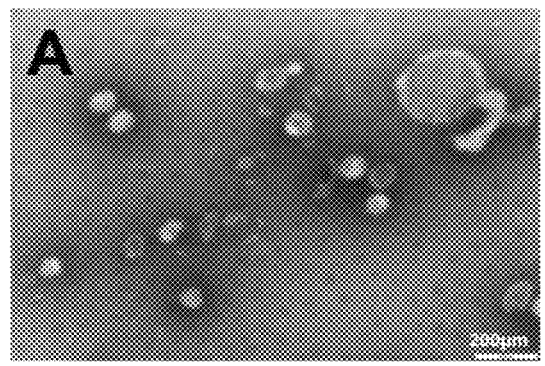
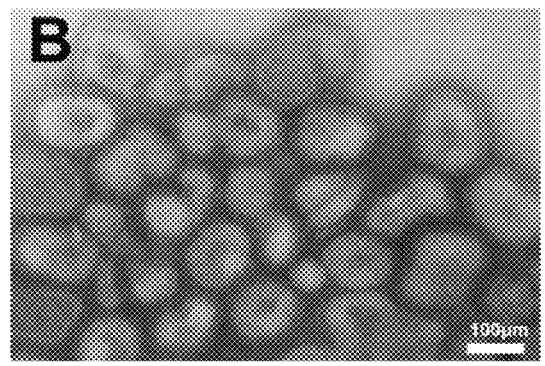

FIG. 13

TABLE 1. Serum Virus Neutralization Titers

| Vaccine | Pre-vaccination | Pre-Challenge | | Post-Challenge | |
|---|---|---|---|---|---|
| | | Day 15 | Day 28 | Day 7 | Day 10 |
| Naive | <50 | <50 | <50 | <50 | <50 |
| Vaccine | <50 | <50 | <50 | <50 | <50 |
| Vaccine + Alum | <50 | <50 | <50 | <50 | <50 |
| Vaccine + EB | <50 | <50 | <50 | <50 | <50 |
| Gt α H5N9 Serum | >400 | | | | |

FIG. 14B

| Vaccine | Vaccination | Day 15 | Day 28 |
|---|---|---|---|
| PBS (mock) | <20 | <20 | <20 |
| Vaccine alone | <20 | <20 | 40 |
| Vaccine + alum | <20 | <20 | 160 |
| Vaccine + 50uM EB | <20 | <20 | 40 |
| Vaccine + 200uM EB | <20 | <20 | 80 |
| Vaccine + 50uM EBX | <20 | <20 | 40 |
| Vaccine + 200uM EBX | <20 | <20 | 40 |

SEQUENCE LISTING

```
<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Lys Lys Ala Ala Val Ala Leu Leu Pro Ala Val Leu Leu Ala
1               5                   10                  15

Leu Leu Ala Pro
            20

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Region may encompass 0 or 3-10 charged amino
      acids
<220> FEATURE:
<221> NAME/KEY: MOD_RES
<222> LOCATION: (27)..(36)
<223> OTHER INFORMATION: Region may encompass 0 or 3-10 charged amino
      acids
<220> FEATURE:
<223> OTHER INFORMATION: See specification as filed for detailed
      description of substitutions and preferred embodiments

<400> SEQUENCE: 2

Xaa Xaa Xaa Xaa Xaa Xaa Xaa Xaa Xaa Xaa Ala Ala Val Ala Leu Leu
1               5                   10                  15

Pro Ala Val Leu Leu Ala Leu Leu Ala Pro Xaa Xaa Xaa Xaa Xaa Xaa
            20                  25                  30

Xaa Xaa Xaa Xaa
        35

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Lys Lys
1

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Lys Lys Leu Pro Ala Val Leu Leu Ala Leu Leu Ala Pro
1               5                   10                  15
```

```
<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Lys Lys Leu Ala Ala Leu Pro Leu Val Leu Ala Ala Pro Leu
1               5                   10                  15

Ala Val Leu Ala
            20
```

PEPTIDE ADJUVANT FOR INFLUENZA VACCINATION

CROSS-REFERENCE TO RELATED APPLICATIONS

This application claims priority from U.S. Provisional Patent Application Ser. No. 61/061,499, filed Jun. 13, 2008, which is herein incorporated by reference in its entirety.

REFERENCE TO A SEQUENCE LISTING

This application includes a Sequence Listing. A paper copy and a computer readable copy of the Sequence Listing are being submitted concurrently herewith. The information contained in the Sequence Listing is herein incorporated by reference in its entirety.

BACKGROUND OF THE DISCLOSURE

The present disclosure generally relates to peptides having adjuvant properties, vaccines comprising the adjuvant peptides, and their use in prophylaxis or therapy for influenza. More particularly, the invention relates to adjuvant peptides that induce aggregation of influenza virus. The peptides can be included in influenza vaccines to increase the immune response to the vaccine.

Outbreaks of influenza A virus continue to cause widespread morbidity and mortality worldwide. In the United States alone, an estimated 5 to 20% of the population is infected by influenza A virus annually, causing approximately 200,000 hospitalizations and 36,000 deaths. The establishment of comprehensive vaccination policies has been an effective measure to limit influenza morbidity. However, the frequent genetic drifting of the virus requires yearly reformulation of the vaccine, potentially leading to a mismatch between the viral strain present in the vaccine and that circulating. Thus, antiviral therapies against influenza virus are important tools to limit both disease severity as well as transmission.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. The surface glycoproteins neuraminidase (NA) and hemagglutinin (HA) appear as spikes, 10 to 12 nm long, at the surface of the particles. It is these surface proteins, particularly the hemagglutinin, that determine the antigenic specificity of the influenza subtypes.

Currently available influenza vaccines are either inactivated or live attenuated influenza vaccine, Inactivated flu vaccines are composed of three possible forms of antigen preparation: inactivated whole virus, sub-virions where purified virus particles are disrupted with detergents or other reagents to solubilize the lipid envelope (so-called "split" vaccine) or purified HA and NA (subunit vaccine). These inactivated or live attenuated vaccines are typically given intramuscularly (i.m.) or intranasally (i.n.).

Split or subunit injectable vaccines are prepared by disrupting the virus particle, generally with an organic solvent or a detergent, and separating or purifying the viral proteins to varying extents. Split vaccines are prepared by fragmentation of whole influenza virus, either infectious or inactivated, with solubilizing concentrations of organic solvents or detergents and subsequent removal of the solubilizing agent and some or most of the viral lipid material. Split vaccines generally contain contaminating matrix protein and nucleoprotein and sometimes lipid, as well as the membrane envelope proteins. Split vaccines will usually contain most or all of the virus structural proteins although not necessarily in the same proportions as they occur in the whole virus. Subunit vaccines on the other hand consist essentially of highly purified viral surface proteins, hemagglutinin and neuraminidase, which are the surface proteins responsible for eliciting the desired virus neutralizing antibodies upon vaccination.

Influenza vaccines, of all kinds, are usually trivalent vaccines. They generally contain antigens derived from two influenza A virus strains and one influenza B strain. A standard 0.5 ml injectable dose in most cases contains 15 μg of hemagglutinin antigen component from each strain, as measured by single radial immunodiffusion (SRD). The influenza virus strains to be incorporated into influenza vaccine each season are determined by the World Health Organization in collaboration with national health authorities and vaccine manufacturers.

One drawback to administration of influenza vaccines comprising inactivated virus is that such vaccines must typically be given in high concentrations in order to bring about a significant increase of antibodies. The administration of inactivated influenza virus or antigen in convenient commercial doses, free of side effects, does not always produce a satisfactory immune response, particularly when administered nasally or orally. As such, it is often necessary to include an adjuvant in the vaccine composition.

Recently, it has been shown that a 20-amino acid peptide derived from the fibroblast growth factor 4 (FGF-4) signal sequence and designated entry blocker (EB), displays significant broad-spectrum activity against influenza viruses in vitro and in vivo. The EB peptide has been described in Jones, et al., "Inhibition of Influenza Virus Infection by a Novel Antiviral Peptide That Targets Viral Attachment to Cells, *Journal of Virology,* (2006) Vol. 80(24), p. 11960-11967, and in U.S. Patent Application Publ. No. 2005/0130884 to Brandt, et al. and in U.S. Patent Application Publ. No. 2005/0203024 also to Brandt, et al. Specifically, it has been demonstrated that in vitro, EB inhibits virus replication at concentrations of 10 μM or greater. In BALB/c mice, EB prevented clinical signs of H5N1 influenza virus infection and increased survival when administered pre- or post-infection. It has also been established that EB inhibited influenza virus attachment to cells.

It has now been discovered that the EB peptide also acts as an effective influenza vaccine adjuvant by inducing viral aggregation, leading to increased viral uptake and processing by antigen presenting cells.

SUMMARY OF THE DISCLOSURE

The present disclosure generally relates to peptides having adjuvant properties, vaccines comprising the adjuvant peptides, and their use in prophylaxis or therapy for influenza. More particularly, the invention relates to adjuvant peptides that induce aggregation of influenza virus. The peptides can be included in influenza vaccines to increase the immune response to the vaccine.

In one aspect, the present disclosure is directed to a vaccine comprising an immunogen and an adjuvant peptide having the formula:

(SEQ ID NO: 2)

$(X1)_n$-A-A-V-A-L-L-P-A-V-L-L-A-L-L-A-P-$(x2)_m$, wherein X1 and X2 are selected from one or more charged amino acid residues, each X1 and each X2 may be the same or different charged amino acid residues, n is 0 or 3-10, and m is 0 or 3-10, but wherein m and n are not both 0; and wherein the immunogen is capable of eliciting an immune response against a respiratory virus.

In another aspect, the present disclosure is directed to a method of immunizing a mammal against a viral respiratory infection, the method comprising administering to the mammal a vaccine comprising an immunogen and an adjuvant peptide having the formula:

$$(X1)_n\text{-A-A-V-A-L-P-A-V-L-L-A-L-L-A-P-}(X2)_m, \quad \text{(SEQ ID NO: 2)}$$

wherein X1 and X2 are selected from one or more charged amino acid residues, each X1 and each X2 may be the same or different charged amino acid residues, n is 0 or 3-10, and m is 0 or 3-10, but wherein m and n are not both 0; and wherein the immunogen is capable of eliciting an immune response against a respiratory virus.

BRIEF DESCRIPTION OF THE DRAWINGS

FIG. 2 is a picture from an electron microscope of PR/8 virions that were mock treated (PBS—0 μM peptide) (FIG. 2A) or treated with 10 μM EB peptide (FIG. 2B), as described in Example 1.

FIG. 13 is a table depicting the results of a microneutralization assay on blood obtained from mice prior to vaccination or on day 15 and day 28 post-vaccination (i.e., pre-challenge serum) and day 7 and day 10 post-challenge with VN/1203 virus, as discussed in Example 5. The mice were vaccinated with either PBS (naive), a suboptimal dose of inactivated VN/1203 virus alone, a suboptimal dose of inactivated VN/1203 virus plus alum, or a suboptimal dose of inactivated VN/1203 virus pretreated with 200 µM EB peptide. Goat anti-H5N9 influenza virus serum was used as a positive control.

FIG. 14B is a table depicting the results of a microneutralization assay on blood obtained from mice prior to vaccination or on day 15 and day 28 post-vaccination (i.e., pre-challenge serum), as discussed in Example 6. The mice were vaccinated with either PBS (mock), a suboptimal dose of inactivated PR/8 virus alone, a suboptimal dose of inactivated PR/8 virus plus alum, or a suboptimal dose of inactivated PR/8 virus pretreated with either 50 µM or 200 µM EB peptide or 50 µM or 200 µM EBX peptide.

DETAILED DESCRIPTION OF THE DISCLOSURE

Figure 1A:
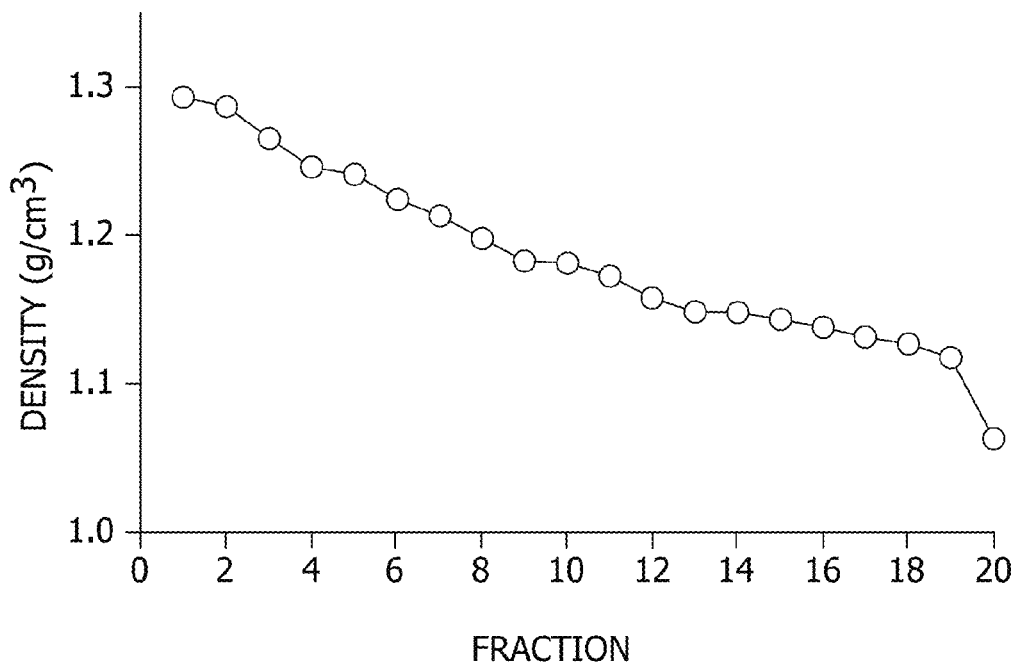
FIG. 1A is a graph depicting the density of gradients obtained through density gradient ultracentrifugation, as described in Example 1.
Figure 1B:
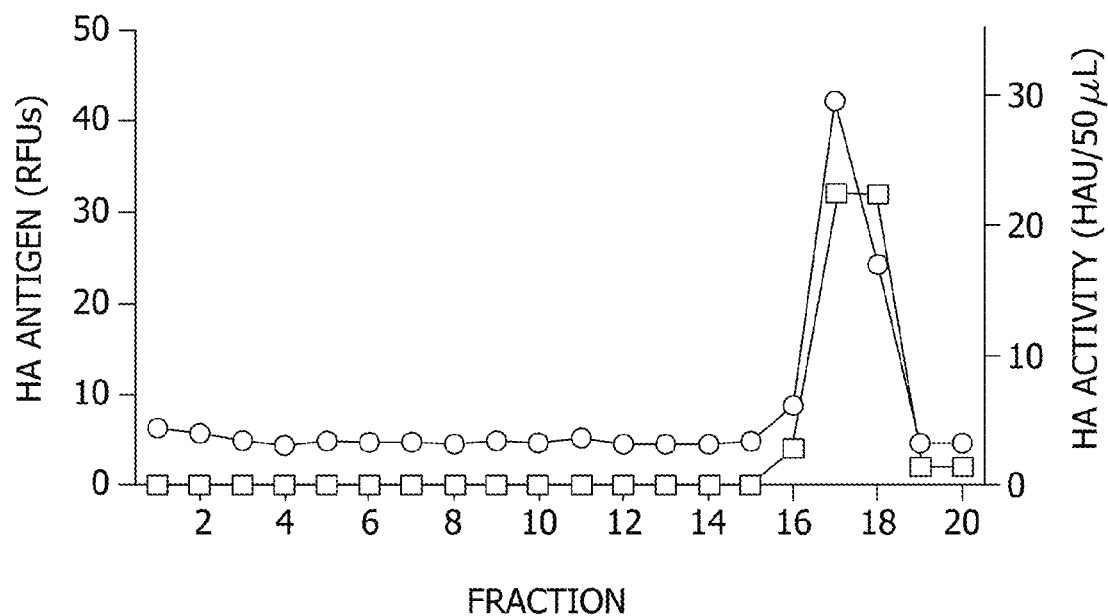
FIG. 1B is a graph depicting the results of density gradient ultracentrifugation for samples of virus treated with PBS (0 μM peptide), as described in Example 1. The presence of HA antigen as determined by immunoblotting is depicted by (○) and hemagglutinating activity is depicted by (□).
Figure 1C:
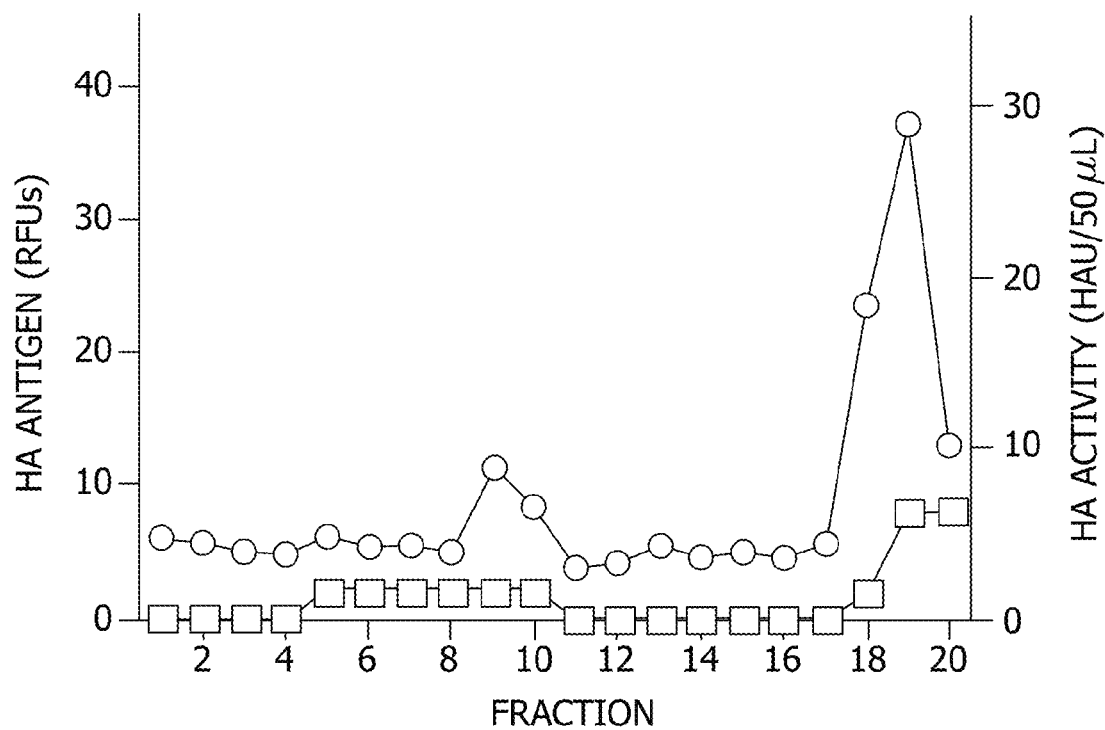
FIG. 1C is a graph depicting the results of density gradient ultracentrifugation for samples of virus treated with 10 μM of EB peptide, as described in Example 1. The presence of HA antigen as determined by immunoblotting is depicted by (○) and hemagglutinating activity is depicted by (□).
Figure 1D:
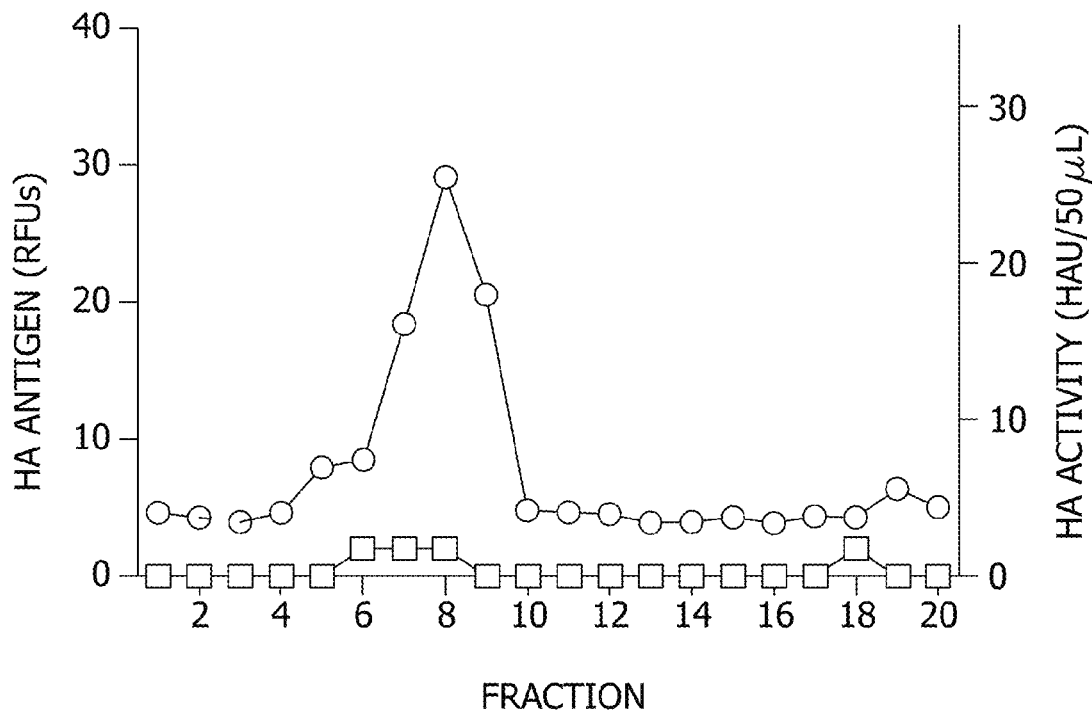
FIG. 1D is a graph depicting the results of density gradient ultracentrifugation for samples of virus treated with 30 μM of EB peptide, as described in Example 1. The presence of HA antigen as determined by immunoblotting is depicted by (○) and hemagglutinating activity is depicted by (□).

The present disclosure generally relates to peptides having adjuvant properties, vaccines comprising the adjuvant peptides, and their use in prophylaxis or therapy for influenza. More particularly, the invention relates to adjuvant peptides that induce aggregation of influenza virus. The peptides can be included in influenza vaccines to increase the immune response to the vaccine.

Definitions

Pharmaceutically acceptable carrier: An acceptable vehicle for administering a vaccine to mammals comprising one or more non-toxic excipients which do not react with or reduce the effectiveness of the pharmacologically active agents (e.g., immunogens, adjuvant peptides, etc.) contained therein.

Solubility tag: A short peptide sequence comprised of charged amino acids which, when attached to a terminal residue of a longer insoluble peptide sequence, will improve solubility in an aqueous medium. In some embodiments the charged amino acids of the solubility tags are exclusively positively charged amino acids, including, but not limited to, ornithine, lysine, and arginine. Solubility tags may be 2 to 24 amino acids long or longer, and typically can be 4, 5, 6, 7, 8, 9, 10, 11, 12, 13, 14, 15, or 16 amino acids long. A solubility tag may be attached to either terminus or both termini of the longer insoluble peptide.

Antigen: An entity that is bound by an antibody or receptor.

Immunogen: An entity that induces an immune response, i.e., induces an innate or an adaptive host response that protect the host from infection. As used herein, the term "immunogen" can include an antigen.

Peptide: The words "polypeptide" and "peptide" are used herein interchangeably throughout the specification and designate a linear series of amino acid residues connected one to the other by peptide bonds between the alpha-amino and carboxy groups of adjacent amino acids. Polypeptides can be a variety of lengths, either in their neutral (uncharged) forms or in forms that are salts. It is well understood in the art that amino acid residue sequences may contain acidic and basic groups, and that the particular ionization state exhibited by the peptide is dependent on the pH value of the surrounding medium when the peptide is in solution, or that of the medium from which it was obtained if the peptide is in solid form. Thus, "polypeptide" or its equivalent terms is intended to include the appropriate amino acid residue sequence referenced. A peptide or polypeptide is always shown herein from left to right and in the direction from amino-terminus (N-terminus) to carboxy-terminus (C-terminus).

Residue: The term "residue" is used interchangeably with the phrase amino acid residue. The amino acids of the peptides described herein may be either levo ("l") amino acids or dextro ("d") amino acids. Any of the peptides described herein can have peptide backbones made up of d amino acids. The following standard one letter abbreviated names for the amino acids are used hereinafter: alanine (A), lysine (K), leucine (L), proline (P), arginine (R), and valine (V).

Effective adjuvant amount: The term "effective adjuvant amount" refers to an amount of an adjuvant peptide of the present disclosure which is capable of stimulating an immune response to an administered immunogen. This may be an amount of adjuvant peptide that increases the immune response to an administered immunogen, as measured in terms of the virus specific IgG levels in the blood at 28 days post administration as compared to the same immunogen administered without any adjuvant peptide. Alternately, the "effective adjuvant amount" may be an amount of adjuvant peptide that does not increase virus specific IgG levels, but results in an increase in T cells or triggers an innate immune response.

The present disclosure is directed to peptides having adjuvant properties, vaccines comprising the adjuvant peptides, and the use of the adjuvant peptides in prophylaxis or therapy for influenza. In particular, it has been discovered that the EB peptide is an effective vaccine adjuvant when included in influenza vaccines. As noted above, EB is a 20-amino acid peptide derived from a fibroblast growth factor, which contains sixteen hydrophobic amino acids, with a highly charged tetrapeptide (RRKK) added to the N-terminus to enhance solubility. EB has the sequence RRKKAAVALLPAVLLALLAP (SEQ ID NO: 1). EB has previously been demonstrated to display antiviral activity against influenza viruses by inhibiting virus binding to host cells. See Jones, et al., *Journal of Virology*, (2006) Vol. 80(24), pp. 11960-11967.

It has now been discovered that EB is also an effective adjuvant for influenza vaccines. Without wishing to be bound to any particular theory, it is believed that one mechanism by which EB may act as an adjuvant is by inhibiting the attachment of influenza virions to host cells by inducing aggregation of intact influenza virions, thus preventing the virus from infecting the host cell. This ability to aggregate influenza virion results in concentration of large volumes of virus at the site of inoculation. These large volumes of virus are believed to signal phagocytic cells, such as dendritic cells and macrophages, to engulf the aggregated influenza virions, initiating an immune response to the vaccine.

Thus, in one aspect, the present disclosure is directed to a vaccine comprising an adjuvant peptide and an immunogen capable of eliciting an immune response against a respiratory virus.

The adjuvant peptide may be any peptide that induces aggregation of influenza virions. In a preferred embodiment, the adjuvant peptide is the EB peptide (SEQ ID NO: 1).

As noted above, the adjuvant peptides of the present disclosure, such as EB, may include a solubility tag (RRKK) covalently attached to a sequence of hydrophobic amino acids. Optionally, the adjuvant peptides of the present disclosure may also comprise other solubility tags covalently attached thereto. For instance, in one embodiment, the adjuvant peptide has the following sequence:

$(X1)_n$-AAVALLPAVLLALLAP-$(x2)_m$ (SEQ ID NO: 2), wherein X1 and X2 are selected from one or more charged amino acid residues (e.g. K, R), where each X1 and each X2 may be the same or different charged amino acid residue; n has a value of 0 or 3-10, and m has a value of 0 or 3-10, but wherein m and n are not both 0. In one embodiment either m=0 or n=0. As noted above, one example of a solubility tag is R-R-K-K (SEQ ID NO: 3). In a preferred embodiment, all of the charged amino acid residues of the solubility tag are positively charged amino acid residues.

The adjuvant peptides of the present invention may also have various reactive tags attached to their terminal amino acid residues. Such tags may be useful in detection and/or removal of the synthetic peptides of the present disclosure. Such tags may include, by way of example only, biotin, dyes such as Cy3, Cy5, or Cy3.5, as well as any other tags well-known in the art.

Certain derivatives of the adjuvant peptides of the present invention may also be useful as adjuvant peptides. Derivatives of the adjuvant peptides are peptides wherein one or more of the amino acid residues are deleted to yield fragments or are substituted for other amino acid residues. Substitutions may be conservative or may be sequence rearrangements. Conservative substitutions are well known to those of skill in the art; amino acids of similar or identical charge, size or hydrophobicity may be substituted for each other. For example, lysine and arginine are conservative substitutions for each other, as are aspartic and glutamic acids, phenylalanine, tyrosine, and tryptophan, and so forth. Rearranged sequences are those in which one or more amino acids are moved from their original position to a new position within the sequence of the peptide.

Adjuvant peptide fragments of the invention can have deletions of 1, 2, 3, 4, 5, 6, 7, 8, 9, 10, 11, 12 or more amino acids, and substituted derivatives can have 1, 2, 3, 4, 5, 6, 7, 8, 9, 10 or more substitutions. In some embodiments, derivatives of the adjuvant peptides have both deletions and substitutions.

Substituted peptides or fragments of the peptides must retain adjuvant activity to remain within the scope of the disclosure. The adjuvant peptides according to the present disclosure or derivatives thereof can be tested for adjuvant activity via the methodology described in the following Examples.

The adjuvant peptides of the present disclosure can also be provided as pharmaceutically acceptable salts. A "pharmaceutically acceptable salt" includes a salt with an inorganic base, organic base, inorganic acid, organic acid, basic amino acid, or acidic amino acid. As salts of inorganic bases, the disclosure includes, for example, alkali metals such as sodium or potassium; alkaline earth metals such as calcium and magnesium or aluminum; and ammonia. As salts of organic bases, the disclosure includes, for example, trimethylamine, triethylamine, pyridine, picoline, ethanolamine, diethanolamine, and triethanolamine. As salts of inorganic acids, the instant disclosure includes, for example, hydrochloric acid, hydroboric acid, nitric acid, sulfuric acid, and phosphoric acid. As salts of organic acids, the instant disclosure includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant disclosure includes, for example, arginine, lysine and ornithine. Acidic amino acids include, for example, aspartic acid and glutamic acid.

The adjuvant peptides of the present disclosure can be prepared by processes which incorporate methods commonly used in peptide synthesis such as classical solution coupling of amino acid residues and/or peptide fragments, and, if desired, solid phase techniques. Any method for peptide synthesis well known in the art may be used, for example, Schroeder and Lubke, in "The Peptides", Vol. 1, Academic Press, New York, N.Y., pp. 2-128 (1965); "The Peptides: Analysis, Synthesis, Biology", (E. Gross et al., Eds.), Academic Press, New York, N.Y., Vol. 1-8, (1979-1987); Stewart and Young, in "Solid Phase Peptide Synthesis", 2nd Ed., Pierce Chem. Co., Rockford, Ill. (1984); Wild et al., Proc. Natl. Acad. Sci. USA, 89: 10537 (1992); and Rimsky et al., *J Virol*, 72: 986 (1998); Chan & White in "Fmoc Solid Phase Peptide Synthesis: A Practical Approach", Oxford University Press, (2000).

The present adjuvant peptides have been found to exhibit adjuvant activity, i.e., improve the protection against a virus provided by an influenza vaccine, against respiratory viruses, including various types of influenza, such as influenza A, influenza B, and influenza C. Advantageously, the adjuvant peptides of the present disclosure exhibit adjuvant activity against both seasonal and avian influenza (e.g., H5N1 strains). Illnesses resulting from infections by these viruses can also be treated according to some of the present methods.

The vaccines of the present disclosure will advantageously comprise an adjuvant peptide in an effective adjuvant amount. As will be apparent to one skilled in the art, the optimal concentration of the adjuvant peptide or peptides will necessarily depend upon the specific peptide(s) used, the characteristics of the patient, the immunogen used, and the nature of the viral infection for which the treatment or prophylaxis is sought. These factors can be determined by those of skill in the medical and pharmaceutical arts in view of the present disclosure. In general, the adjuvant peptides are most desirably administered at a concentration level that will generally afford adjuvant activity without causing any harmful or deleterious side effects. Generally, an effective adjuvant amount is desired. An effective adjuvant amount refers to an amount of an adjuvant peptide which is capable of stimulating an immune response to an administered immunogen.

Specific dosages may be adjusted depending on conditions of disease, the age, body weight, general health conditions, sex, diet of the subject, dose intervals, administration routes, excretion rate, and combinations of drugs. Any of the dosage forms described herein containing effective amounts are well within the bounds of routine experimentation and therefore, well within the scope of the instant disclosure.

In addition to the adjuvant peptide, the vaccines of the present disclosure further comprise an immunogen that is capable of eliciting an immune response against a respiratory virus such as influenza virus. In one embodiment, the immunogen is an antigen. In another embodiment, the immunogen may be DNA molecules (polynucleotides) which produce the antigen in cells after introduction of the DNA molecule to the cells (e.g. by transfection). The DNA is not itself an "antigen" but it may encode the antigen and is thus an immunogen, as used herein.

The antigen may be a live attenuated virus, a non-live flu antigen, or a combination thereof. A non-live flu antigen for use in the present disclosure may be selected from the group consisting of split virus antigens, subunit antigens (either recombinantly expressed or prepared from whole virus), and/or inactivated whole virus which may be chemically inactivated by any suitable means including, for example, by treating with formaldehyde, formalin, β-propiolactone, or otherwise inactivated such as by ultraviolet or heat inactivation. Preferably the antigen is an inactivated whole virus.

Examples of suitable antigens may also include, for example, proteins from pathogens, recombinant proteins, peptides, polysaccharides, glycoproteins, and lipopolysaccharides.

The immunogen may be provided in a purified or an unpurified form. Preferably, the immunogen is provided in a purified form.

The vaccine according to the invention may contain both A and B strain virus immunogens, and typically is a trivalent composition of two A strains and one B strain. However, divalent and monovalent vaccines are not excluded. Monovalent vaccines may be advantageous in a pandemic situation, for example, where it is important to get as much vaccine produced and administered as quickly as possible.

Preferably the concentration of immunogen for each strain of the influenza virus for inclusion in the vaccine is an amount which induces an immune response without significant, adverse side effects. Such amount will vary depending on which immunogen is used and the type and amount of adjuvant peptide included in the vaccine. Typically, a vaccine will comprise immunogen in an amount of from about 1 to about 1000 µg per ml, more preferably from about 3 to about 300 µg per ml and most preferably about 10 µg to about 15 µg per ml, as measured by a SRD assay. Following an initial vaccination, subjects being vaccinated may receive one or several booster immunizations adequately spaced thereafter.

Advantageously, it has been discovered that the adjuvant peptides of the present disclosure will enhance the immunogenicity of a vaccine composition comprising even relatively low amounts of immunogen, providing antigen sparing. As such, in one embodiment, the vaccine of the present disclosure will comprise immunogen in an amount of less than about 10 µg per ml, or from about 1 µg to about 10 µg per ml, or from about 1 µg to about 5 µg per ml. In one embodiment, the vaccine comprises immunogen in an amount of about 1 µg per ml.

The influenza virus immunogen may be derived from the conventional embryonated egg method, or may be derived from any methods using tissue culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells. Suitable cell substrates are not limited to cell lines; for example primary cells such as chicken embryo fibroblasts are also included.

In one embodiment, the virus antigen is obtained from an infected cell culture, such as described in the examples. Particularly preferred for the use according to the invention to produce an influenza virus vaccine is an influenza virus immunogen that is obtained from a MDCK cell culture infected with influenza virus that is cultured in a serum and protein-free medium. The virus immunogen obtained from the infected cell culture is first inactivated with formalin and can then be obtained as a purified, concentrated virus immunogen by means of continuous density gradient centrifugation. This preparation can then be used together with the adjuvant peptides of the present disclosure to produce an influenza vaccine.

A special advantage in the production of the vaccine is that the virus material may be inactivated before purification, and so in comparison to the purification of attenuated live viruses, a considerably higher degree of purity of the immunogen may be achieved.

A particular advantage in the use of influenza virus immunogens obtained from a serum and protein-free cell culture infected with influenza virus is the absence of egg-specific proteins that could trigger an allergic reaction against these proteins. Therefore, the use according to the disclosure is especially suitable for the prophylaxis of influenza virus infections, particularly in populations that constitute higher-risk groups, such as asthmatics, those with allergies, and also people with suppressed immune systems and the elderly.

The influenza virus immunogen may also be produced by any of a number of commercially applicable processes, for example a split flu process. Traditionally split flu is produced using a solvent/detergent treatment, such as tri-n-butyl phosphate, or diethylether in combination with Tween™ (known as "Tween-ether" splitting). Other splitting agents now employed include detergents or proteolytic enzymes or bile salts, for example sodium deoxycholate. Detergents that can be used as splitting agents include cationic detergents e.g., cetyl trimethyl ammonium bromide (CTAB), other ionic detergents e.g., laurylsulfate, taurodeoxycholate, or non-ionic detergents such as the ones described above including Triton X-100 and Triton N-101, or combinations of any two or more detergents.

The preparation process for a split vaccine will include a number of different filtration and/or other separation steps such as ultracentrifugation, ultrafiltration, zonal centrifugation and chromatography (e.g ion exchange) steps in a variety of combinations, and optionally an inactivation step, e.g., with heat, formaldehyde or β-propiolactone or ultraviolet which may be carried out before or after splitting. The splitting process may be carried our as a batch, continuous or semi-continuous process.

Preferred split flu vaccine immunogen preparations according to the invention comprise a residual amount of Tween 80 and/or Triton X-100 remaining from the production process, although these may be added or their concentrations adjusted after preparation of the split immunogen. Preferably both Tween 80 and Triton X-100 are present. The preferred ranges for the final concentrations of these non-ionic surfactants in the vaccine dose are: Tween 80:0.01 to 1% (v/v), more preferably about 0.1% (v/v); Triton X-100:0.001 to 0.1 (% w/v), more preferably 0.005 to 0.02% (w/v).

Alternatively the influenza virus immunogen may be derived from a source other than the live influenza virus, for example the hemagglutinin, matrix, neuraminidase, or nucleoprotein antigen may be produced recombinantly.

In addition to immunogen and adjuvant peptides, the vaccines of the present disclosure may further comprise one or more suitable pharmaceutically acceptable carrier, the proportion of which is determined by the solubility and chemical nature of the adjuvant peptide and immunogen, the chosen route of administration, and standard biological administration. Suitable pharmaceutically acceptable carriers for the vaccines of the present disclosure are described in the standard pharmaceutical texts. See, e.g., "Remington's Pharmaceutical Sciences", 18th Ed., Mack Publishing Company, Easton, Pa. (1990). Specific non-limiting examples of suitable pharmaceutically acceptable carriers include water, saline, dextrose, glycerol, ethanol, or the like and combinations thereof.

In addition, if desired, the vaccine can further contain minor amounts of auxiliary substances such as agents that enhance the antiviral effectiveness of the composition, stabilizers, preservatives, and the like.

In one embodiment, the vaccine may also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particularly preferred example is sodium deoxycholate (NaDOC) which may be present in the final vaccine dose.

Optionally, the vaccines may further comprise an adjuvant in addition to the adjuvant peptides described herein. Suitable adjuvants for inclusion in compositions of the present disclosure include those that are well known in the art, such as complete Freund's adjuvant (CFA) that is not used in humans, incomplete Freund's adjuvant (IFA), squalene, squalane, alum, and various oils, all of which are well known in the art, and are available commercially from several sources, such as Novartis (e.g., Novartis' MF59 adjuvant).

Depending on the route of administration, the vaccine may take the form of a solution, suspension, emulsion, or the like.

A vaccine of the present disclosure can be administered intranasally or through parenteral administration, such as through sub-cutaneous injection, intra-muscular injection, intravenous injection, intraperitoneal injection, or intra-dermal injection to a mammal, e.g., humans, horses, other mammals, etc. Typically, the vaccine is administered through intramuscular or intradermal injection. One or more adjuvant peptides can be included in the vaccines described herein.

For parenteral administration, the vaccines of the present disclosure may be administered by intravenous, subcutaneous, intramuscular, intraperitoneal, or intradermal injection. The vaccine may comprise only immunogen and adjuvant peptide, or optionally may further comprise pharmaceutically accepted carriers. For administration by injection, it is preferred for the vaccine to be a solution in a sterile aqueous vehicle which may also contain other solutes such as buffers or preservatives as well as sufficient quantities of pharmaceutically acceptable salts or of glucose to make the solution isotonic. The adjuvant peptides of the present disclosure can be obtained in the form of therapeutically acceptable salts that are well-known in the art.

Because the adjuvant peptides of the present disclosure have shown adjuvant activity in vaccines for respiratory viruses, the vaccine can also be delivered locally to the respiratory system, for example to the nose, sinus cavities, sinus membranes or lungs. The vaccine containing the adjuvant peptide, can be delivered to the respiratory system in any suitable manner, such as by inhalation via the mouth or intranasally. The vaccines can be dispensed as a powdered or liquid nasal spray, suspension, nose drops, a gel or ointment, through a tube or catheter, by syringe, by packtail, by pledget, or by submucosal infusion. The vaccines may be conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the vaccine and a suitable powder base such as lactose or starch. Examples of intranasal formulations and methods of administration can be found in PCT publications WO 01/41782, WO 00/33813, and U.S. Pat. Nos. 6,180,603; 6,313,093; and 5,624,898. The latter-cited U.S. patents are incorporated herein by reference and for all purposes. A propellant for an aerosol formulation may include compressed air, nitrogen, carbon dioxide, or a hydrocarbon based low boiling solvent. The vaccines of the present disclosure can be conveniently delivered in the form of an aerosol spray presentation from a nebulizer or the like. In some aspects, the active ingredients (i.e., immunogens, adjuvant peptides, etc.) are suitably micronised so as to permit inhalation of substantially all of the active ingredients into the lungs upon administration of the dry powder formulation, thus the active ingredients will have a particle size of less than 100 microns, desirably less than 20 microns, and preferably in the range 1 to 10 microns. In one embodiment, the vaccine is packaged into a device that can deliver a predetermined, and generally effective, amount of the vaccine via inhalation, for example a nasal spray or inhaler.

According to a further aspect of the disclosure, there is provided a method of immunizing a mammal against a viral respiratory infection, the method comprising administering to the mammal a vaccine comprising an immunogen which is capable of eliciting an immune response against a respiratory virus and an adjuvant peptide of the present disclosure.

The vaccines are preferably administered prophylactically. For instance, administration of the vaccine may be commenced before or at the time of infection or at the time the mammal is exposed to a respiratory virus, and optionally continued until virus is no longer present or active in the respiratory tract. In one embodiment, the vaccines are administered at least one week prior to exposure to the respiratory virus. In other embodiments, the vaccines may be administered at least two weeks, or at least one month prior to exposure to the respiratory virus.

The desired vaccine dose may be presented in a single dose or as divided doses administered at appropriate intervals, for example as two, three, four or more sub-doses per day. Optionally, a dose of vaccine may be administered on one day, followed by one or more booster doses spaced as desired thereinafter, although booster doses are not required for the vaccine to protect against infection. In one exemplary embodiment, an initial vaccination is given, followed by a boost of the same vaccine approximately one week to 15 days later.

The present disclosure is further described with reference to the following illustrated Examples. Unless defined otherwise, all technical and scientific terms used herein have the same meaning as commonly illustrated by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well-known to one of ordinary skill in the art. The materials, methods and Examples are illustrative only and not limiting. All references cited herein are incorporated by reference.

Having described the disclosure in detail, it will be apparent that modifications and variations are possible without departing from the scope of the disclosure defined in the appended claims.

EXAMPLES

The following non-limiting examples are provided to further illustrate the present disclosure.

Test Methods

Cell culture and virus: A/Vietnam/1203/04 (VN/1203, H5N1) and A/PuertoRico/8/34 (PR/8, H1N1) were propagated in 10 day-of-age specific pathogen-free embryonated chicken eggs (Sunnyside Farms, Beaver Dam, Wis.) at 37° C. for 24 to 48 hours. The allantoic fluid was harvested, centrifuged for clarification, and stored at −70° C. until needed for purification. VN/1203 for animal challenge was propagated in Madin-Darby canine kidney cells (MDCK, ATCC, Manassas, Va.), and culture supernatants were harvested 48 to 72 hours post infection (hpi), centrifuged for clarification, and stored at −70° C. Viral titers were determined by fifty percent tissue culture infectious dose ($TCID_{50}$) analysis in MDCK cells, and evaluated by the method of Reed and Muench, *Am. J. Hyg.*, Vol. 27, pp. 493-497 (1938). MDCK cells were cultured in modified Eagle's medium (MEM, CellGro, Herndon, Va.) supplemented with 2 mM glutamine and 10% fetal bovine serum (FBS, Gemini Bio-Products, West Sacramento, Calif.) at 37° C., 5.5% $CO_2$. RAW264.7 cells were cultured in RPMI 1640 medium (CellGro, Herndon, Va.) supplemented with 1 mM sodium pyruvate and 10% heat inactivated FBS.

Laboratory Facilities: All experiments using H5N1 viruses, including work with animals, were conducted in a U.S. Department of Agriculture and Select Agent Program-certified biosafety level-3 enhanced containment laboratory. Investigators were required to wear appropriate respirator equipment (RACAL, Health and Safety Inc., Frederick, Md.). Mice were housed in HEPA-filtered, negative pressure, vented isolation containers (M.I.C.E.®, Animal Care Systems, Littleton, Colo.).

Virus Inactivation and Purification: Allantoic fluid containing VN/1203 virus was treated with 0.1% formalin (V/V) for 5 days at 4° C. To verify inactivation, 10-day-of-age embryonated chicken eggs or MDCK cells were inoculated with viral stocks and monitored for death and cytopathic effects (CPE) after 48 and 72 hours post infection (hpi), respectively. Inoculated MDCK cells were collected and lystates were used to infect another round of cells. Upon verification of inactivation, virus was purified by overlaying allantoic fluid onto a 30-60% discontinuous sucrose gradient, centrifuged for 90 minutes at 26,000 rpm in a SW-28 rotor, and the virus layer extracted from the 30-60% interface. Virus was then pelleted by centrifugation as described above, resuspended in phosphate buffered saline (PBS), and homogenized with an 18 g needle. Viral titers were determined by hemagglutination (HA) assay and reported as hemagglutinating units per 50 μL (HAU/50 μL), as described in Jones, et al., *Journal of Virology*, 2006, Vol. 80(24), p. 11960-11967.

Virus Labeling: PR/8 virus, purified as described above, was labeled with fluorescein isothiocyanate (FITC-PR/8) using the EZ-Label FITC protein labeling kit (Pierce, Rockford, Ill.) according to manufacturer's instructions. FITC-labeled virus was titered by HA assay.

Peptide synthesis: Synthesis and analysis of the EB peptide (SEQ ID NO: 1) was performed by EZBiolab, Inc. (Westfield, Ind.). Synthesized peptides were purified by HPLC with to purity that met or exceeded 90%.

Sedimentation density profiles: PR/8 virus (512 HA units) was treated with 0 (mock), 10, or 30 μM concentrations of EB peptide for 1 hour at 37° C. and layered on a continuous 20-60% sucrose gradient. Samples were subjected to ultracentrifugation in a Beckman SW-41 at 18,000 rpm for 90 minutes. Samples (500 μL) were collected from the bottom of the tube and 7 μL of each fraction was dotted to nitrocellulose, blocked with 3% milk in Tris-buffered saline containing 0.1% Tween-20 (TTBS) and probed with goat anti-hemagglutinin serum (1:1000 in TTBS) for 1 hour at room temperature, followed by donkey anti-goat IgG (1:2000, Santa Cruz Biotechnology, Santa Cruz, Calif.). Immune complexes were detected by enhanced chemiluminescence (Pierce, Rockford, Ill.). The density of each sucrose fraction was determined by measuring refractive index in a Bausch and Lomb 334610 Refractometer (Rochester, N.Y.).

Electron microscopy: Purified PR/8 virus (512 HA units) was treated with PBS alone (mock) or 10 μM of the EB peptide for 1 hour at 37° C. Samples (10 μl) were adsorbed to poly-L-lysine coated grids for 5 min at 23° C. The grids were rinsed with PBS, stained with 2% phosphotungstic acid (PTA) in water adjusted to pH 6, and air dried. Grids were examined in a JEOL JEM-1200EX electron microscope at magnifications of ×15,000 and ×40,000.

Splenocyte IFN-γ ELISpot Assay: At days 15 and 28 days post vaccination, spleens were collected from 2 to 3 mice per group. To isolate splenocytes, spleens were forced though a 0.7 μm cell strainer and isolated spleen cells were washed with R10 medium (RPMI 1640, 10% heat inactivated fetal bovine serum, 1 mM sodium pyruvate, and 100 I.U penicillin, 100 μg/ml streptomycin). To remove red blood cells, splenocytes were centrifuged and suspended in AKC red blood cell lysis buffer (0.15 M $NH_4Cl$, 1 mM $KHCO_3$, and 0.1 mM EDTA) for 5 min at room temp. Splenocytes were centrifuged, washed and resuspended in R10 medium. IFN-γ ELISpot assay was performed as per manufacturers' instructions (Mabtech, Cincinnati, Ohio). Briefly, isolated splenocytes ($1 \times 10^6$ cells per well) were stimulated for 24 hours with 1 μg formalin inactivated PR/8 virus, 1 μg formalin inactivated VN/1203 virus, CD3 antiserum or 1 μg/ml concavalin A (positive controls) in R10 media and added to individual wells of the ELISpot plate. The number of IFN-γ secreting splenocytes was enumerated using a ELISpot plate reader. All experiments were performed on individual mice in duplicate.

Analysis of Antibody Response by ELISA: Serum was collected from all time points and treated with receptor destroying enzyme (RDE, Denka Seiken, Tokoyo, Japan) as per manufacturer's instructions, and vsIgG was tested by ELISA as described in Lu, et al., "Immunity to influenza A H9N2 viruses induced by infection and vaccination," *J. Virol.*, 2001, Vol. 75(10), p. 4896-901, and Katz, et al., "Adjuvant activity of the heat-labile enterotoxin from enterotoxigenic *Escherichia coli* for oral administration of inactivated influenza virus vaccine," *J. Infect. Dis.,* 1997, Vol. 175(2), p. 352-63, with slight modifications. Briefly, microtiter wells were coated with 100 μL of PBS containing 50 HAU of MDCK grown VN/1203 overnight at 4° C. After washing with PBS containing 0.05% Tween-20 (PBST), non-specific binding sites were blocked with 4% BSA in PBST for 1 hour at room temperature. RDE treated sera was diluted 1:100 in 1% bovine serum albumin (BSA) in PBST, and 100 μL was added to wells for 1 hour at room temperature. Bound IgG was detected by anti-mouse total IgG, IgG1, or IgG2a-specific conjugated streptavidin (1:2000 Jackson Labs, Bar Harbor, Me.) diluted in 1% BSA/PBST for 1 hour at room temperature followed by quantification using tetramethylbenzidine (R&D Systems, Minneapolis, Minn.).

Absorbance was measured on a SpectraMax 250 Spectrophotometer (Molecular Devices, Sunnyvale, Calif.) at A405 nm with an A605 nm correction after a 15 min of incubation.

Analysis of Neutralizing Antibody Response by Microneutralization: Detection of serum neutralizing antibodies was carried as described in Rowe, et al., "Detection of antibody to avian influenza A (H5N1) virus in human serum by using a combination of serologic assays," *J. Clin. Microbiol.*, 1999, Vol. 37(4), p. 937-43, with several modifications. Two-fold dilutions (50 μl volume) of RDE-treated sera were prepared over a concentration range of 1:50-1:400 in assay diluent (1% bovine serum albumen in PBS containing penicillin and streptomycin) in a 96-well plate and incubated with VN/1203 virus (100 $TCID_{50}$) for 2 hours at 37° C. MDCKs cells ($3 \times 10^4$) were added and incubated 18 hours at 37° C., 5% $CO_2$. The cells were fixed with 80% acetone, blocked with assay diluent containing 1% Tween-20, and probed for nucleoprotein (NP) with mouse anti-influenza antibodies (1:4000 final concentration of 1:1 MAB8258 and MAB8257, Millipore, Billerica, Mass.). After extensive washing, goat anti-mouse IgG HRP (1:2000, Jackson Labs, West Grove, Pa.) was added for 1 hour at room temperature followed by color development by quantification using tetramethylbenzidine (R&D Systems, Minneapolis, Minn.). Goat anti-H5N9 serum (BEI Resources, Manassas, Va.) was used as a positive control for neutralization. Titers <50 are considered negative.

Statistical Analysis: All data were performed in triplicate and are representative of at least 3 separate experiments. The results represent the means±standard deviations of triplicate determinations. Statistical significance of the data was determined by using analysis of variance (ANOVA) or Student's t-test, and using GraphPad statistical analysis program.

Example 1

In this example, the ability of the EB peptide to inhibit the attachment of influenza virus to host cells through EB-mediated aggregation of the influenza virion was evaluated.

Density gradient ultracentrifugation was used to isolate potential peptide-induced viral aggregates. PR/8 virus was treated with 0 μM, 10 μM, or 30 μM of EB (SEQ ID NO: 1) for 1 hour at 37° C., and layered onto a continuous 20-60% sucrose gradient, as described above. After centrifugation at 18,000 rpm for 90 minutes, 0.5 mL fractions were collected, spotted onto nitrocellulose, and probed for HA by immunoblotting and densitometery performed to quantitate HA levels. Further, the HA activity of each fraction was determined. The results are shown in FIG. 1. For FIGS. 1B and 1C, the presence of HA antigen in each fraction as determined by immunoblotting is represented by (○) on the first Y axis, and HA activity in each fraction is represented by (□) on the second Y axis.

FIG. 1A illustrates the density of the respective gradients. PR/8 virus alone was present in the fractions containing approximately 30% sucrose with a density of 1.14 g/cm$^3$. These fractions also contained HA activity, demonstrating that the purified virus was active, as can be seen from FIG. 1B, which shows results for virus treated with PBS (0 μM peptide). In contrast, pretreatment with 10 μM EB peptide resulted in a shift in the location of the HA antigen to the 20% to 45% sucrose fractions, as can be seen from FIG. 1C. Pre-treatment with 30 μM EB peptide (see FIG. 1D) caused an even more dramatic shift with HA antigen localized to the 41-53% sucrose with the majority of virus antigen detected at a density of 1.20 g/cm$^3$. More importantly, HA activity was considerably lower in the EB peptide-treated samples as compared to virus alone, indicating that the aggregates were impaired in their ability to attach to cRBCs.

To confirm that the EB peptide induced viral aggregation, purified PR/8 virus (512 HA units) was treated with PBS (mock) or 10 μM of EB for 1 hour at 37° C., and analyzed by electron microscopy, as described above. The results are shown in FIG. 2.

In mock-treated samples (FIG. 2A), individual virions were uniformly scattered across the field, with sporadic aggregates (approximately 2 to 4 virions) noted. In contrast, nearly all of the virions treated with the EB peptide were found in large clusters of 25 to 100 individual viral particles, confirming that EB peptide aggregates influenza virus (FIG. 2B).

Example 2

In this example, the ability of EB to affect the association of influenza virus with macrophages was evaluated.

Purified PR/8 virus (512 total HAU) labeled with fluorescein isothiocyanate (FITC-PR/8) was treated with either 0 μM, 10 μM, 30 μM, or 50 μM of the EB peptide (SEQ ID NO: 1) for 1 hour at 37° C. The virus was then incubated with $2 \times 10^5$ RAW 264.7 macrophages in a total volume of 1 mL of RPMI 1640 containing 1% BSA for 1 hour at 37° C., with gentle rocking. The macrophages were washed twice with PBS and fixed with 1% paraformaldehyde. Virus-cell association was measured on a LSR-II Benchtop flow cytometer (BD Biosciences, Franklin Labs, N.J.). Single cell populations of mock-infected macrophages (PBS only) were gated based on forward and side scatter characteristics, and 5,000 events from each experimental group were recorded. Experiments on all samples were performed in triplicate. The results are shown in FIG. 3.

Figure 3A:
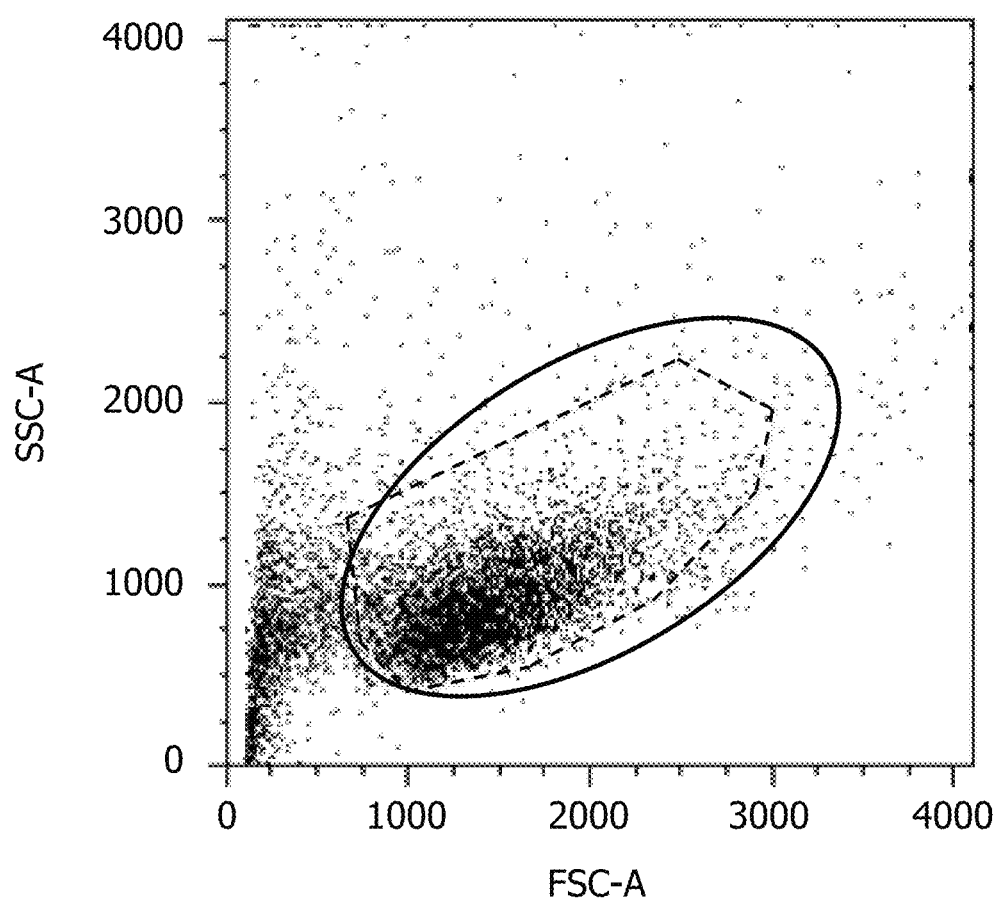
FIG. 3A is a graph depicting single cell populations of $2 \times 10^5$ mock treated macrophages gated based upon forward and side scatter characteristics, as described in Example 2.
Figure 3B:
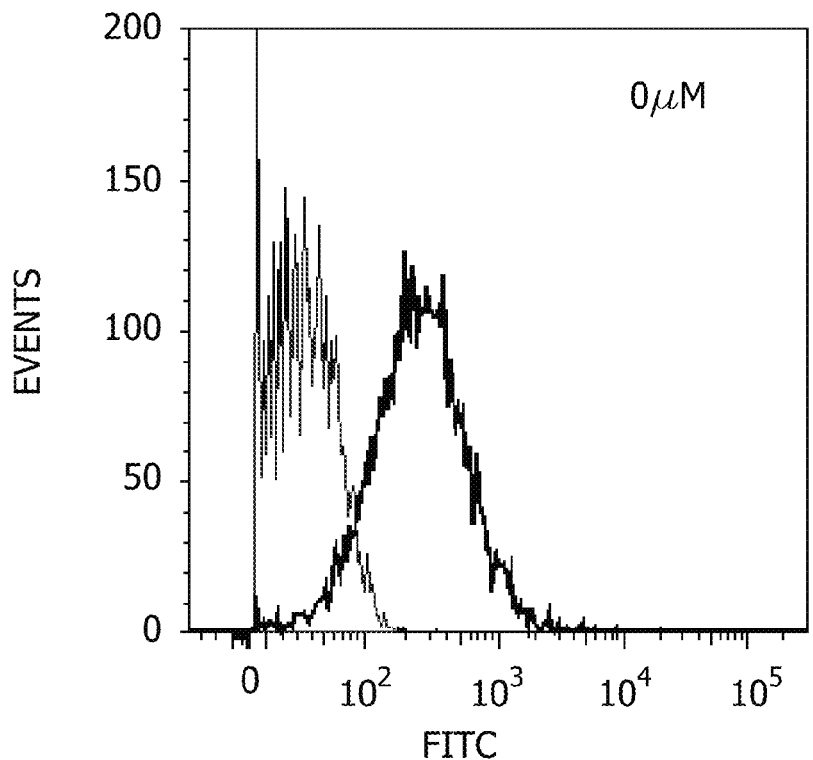
FIGS. 3B to 3E are histograms depicting the association between RAW 264.7 macrophages and FITC labeled influenza virus (heavy line) pretreated with 0 μM EB peptide (FIG. 3B), 10 μM EB peptide (FIG. 3C), 30 μM EB peptide (FIG. 3D), or 50 μM EB peptide (FIG. 3E), as determined by flow cytometry as described in Example 2. The light line in each of FIGS. 3B-3E depicts background fluorescence by PBS-treated macrophagess not exposed to virus.
Figure 3C:
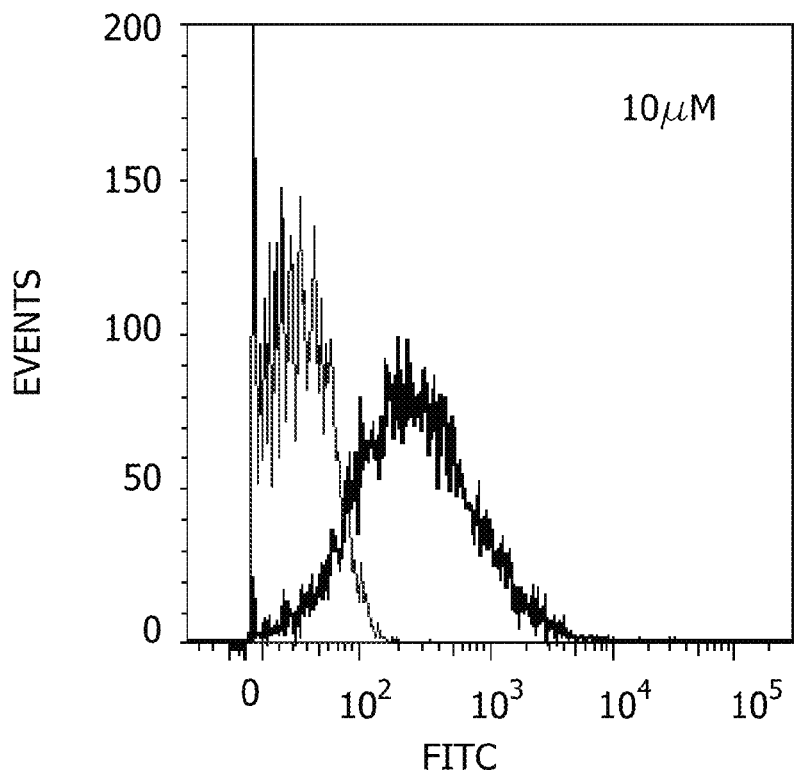
Figure 3D:
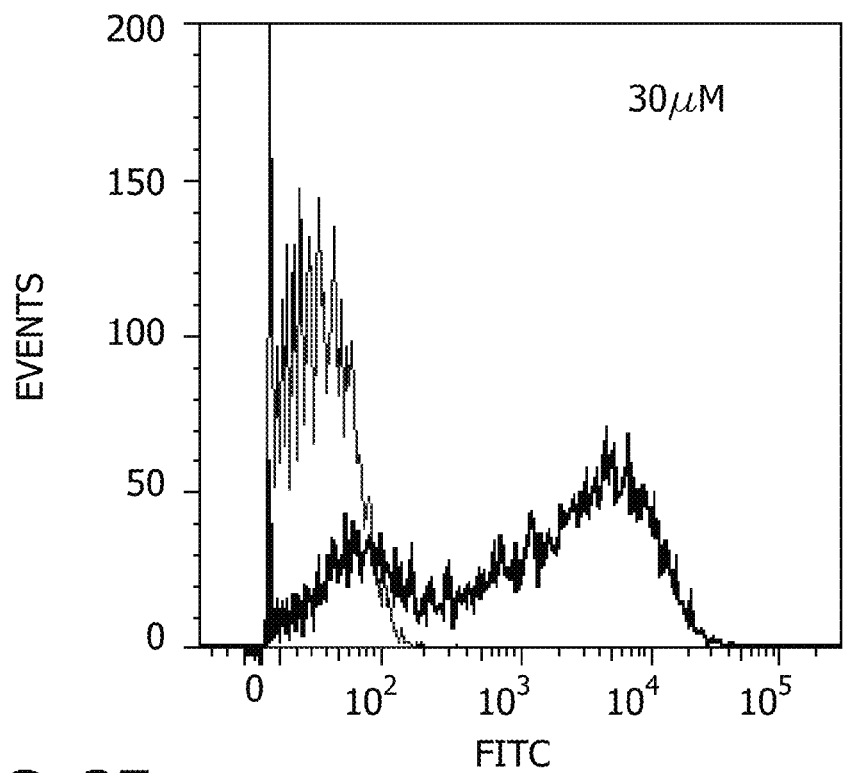
Figure 3E:
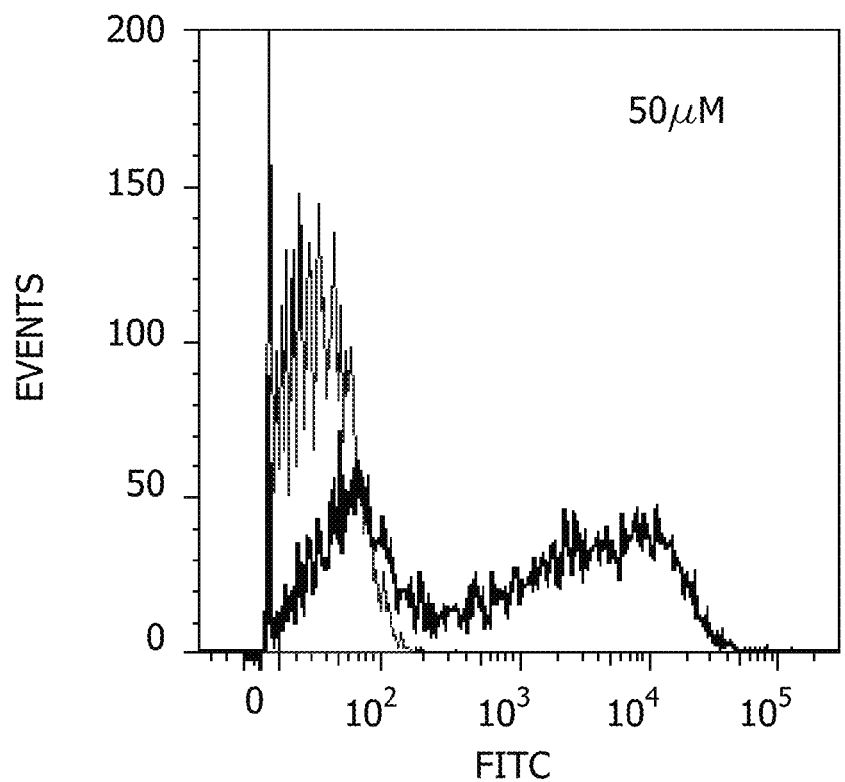

FIG. 3A is a graph depicting single cell populations of $2 \times 10^5$ mock treated RAW 264.7 macrophages gated based upon forward and side scatter characteristics. FIGS. 3B-3E are histograms illustrating the association between the macrophages and FITC-PR/8 that had been pretreated with 0 μM EB (FIG. 3B), 10 μM EB (FIG. 3C), 30 μM EB (FIG. 3D), or 50 μM EB (FIG. 3E). Background fluorescence by PBS treated macrophages is indicated in FIGS. 3B-3E by the light line, and gives a FITC signal of $\leq 10^2$. The heavy line in FIGS. 3B-3E illustrates the association of FITC-PR/8 with macrophages. FIG. 3B illustrates background association of mock treated (0 μM) FITC-PR/8 with macrophages, giving a FITC signal of $\leq 10^3$. When virus was treated with 10 μM EB (FIG. 3C), there was minimal shift in the association peak as compared to FIG. 3B, indicating that this concentration of EB did not increase association with macrophages. In contrast, when virus was treated with 30 μM (FIG. 3D) or 50 μM (FIG. 3E) of EB, an increase in macrophage associated virus was observed as indicated by significant shifts in the association peaks. In these cases, FITC signal of $10^3$ to greater than $10^4$ was observed. Overall cell numbers with associated virus are lower in FIGS. 3D and 3E, as compared to FIG. 3B, represented by a decrease in magnitude of the peaks. However, the FITC signal from these macrophages is considerably higher, suggesting that these macrophages may have taken up larger viral aggregates. Overall, this data indicates that virus treated with concentrations of 30 μM or greater EB shows increased association with macrophages and suggests that virus aggregation induced by the peptide may increase their uptake by phagocytic cells.

Example 3

In this example, the ability of the EB peptide to enhance immunogenicity of an avian influenza vaccine composition in vivo was evaluated.

To begin, vaccine compositions were prepared. Formalin-inactivated sucrose purified VN/1203 virus (1-10 µg total protein, as determined by BCA assay, commercially available from Pierce Biotechnology) was incubated alone, with 0.5 mg/ml aluminum ammonium sulfate (alum), or with 0.5 mM, 1 mM, 10 µM, or 50 µM of the EB peptide (SEQ ID NO: 1) for 1 hr at 37° C. All vaccines were prepared in sterile PBS.

Blood was drawn from the tail vein of four to six weeks of age female Balb/C mice (n=6 per group), followed by hind-limb intramuscular injection with either 50 µL of vaccine preparation or mock vaccination with 50 µL PBS via intramuscular (im) injection in the hind limb on day 0. All mice were bled and received a boost of vaccine or PBS (mock vaccinated) at day 15. Mice were again bled at day 28 post initial vaccination. At 29 days post-initial vaccination, mice were challenged as described below.

Virus specific antibody production: To assess virus specific antibody production, blood was collected from individual mice on days 0, 15, and 28 post-initial vaccination, as described above, and sera was treated with receptor destroying enzyme (RDE, Denka Seiken, Tokyo, Japan) as per the manufacturer's instructions.

Virus specific IgG levels in the sera were determined by ELISA as previously described in Lu, et al., J. Virol., 2001, Vol. 75, p. 4896-4901, and Katz, et al., J. Infect. Dis., 1997, Vol. 175, pp. 352-363, with slight modifications. Briefly, microtiter wells were coated with 100 µL of a 100 HAU/mL solution of tissue culture grown VN/1203 overnight at 4° C. After washing with PBS containing 0.05% Tween-20 (PBST), non-specific binding sites were blocked with 4% BSA in PBST for 1 hr at room temp, and then washed extensively. RDE-treated sera was diluted 1:100 in 1% bovine serum albumin (BSA) in PBST and added to the wells for 1 hour at room temp. Bound IgG was detected by anti-mouse IgG conjugated streptavidin (Jackson Labs, Bar Harbor, Me.) diluted 1:2000 in 1% BSA PBST for 1 hour at room temp followed by quantification using tetramethylbenzidine (R&D Systems, Minneapolis, Minn.). Absorbance was measured on a SpectraMax 250 Spectrophotometer (Molecular Devices, Sunnyvale, Calif.) at A405 nm with an A605 nm correction after 15 minutes of incubation.

Figure 4:
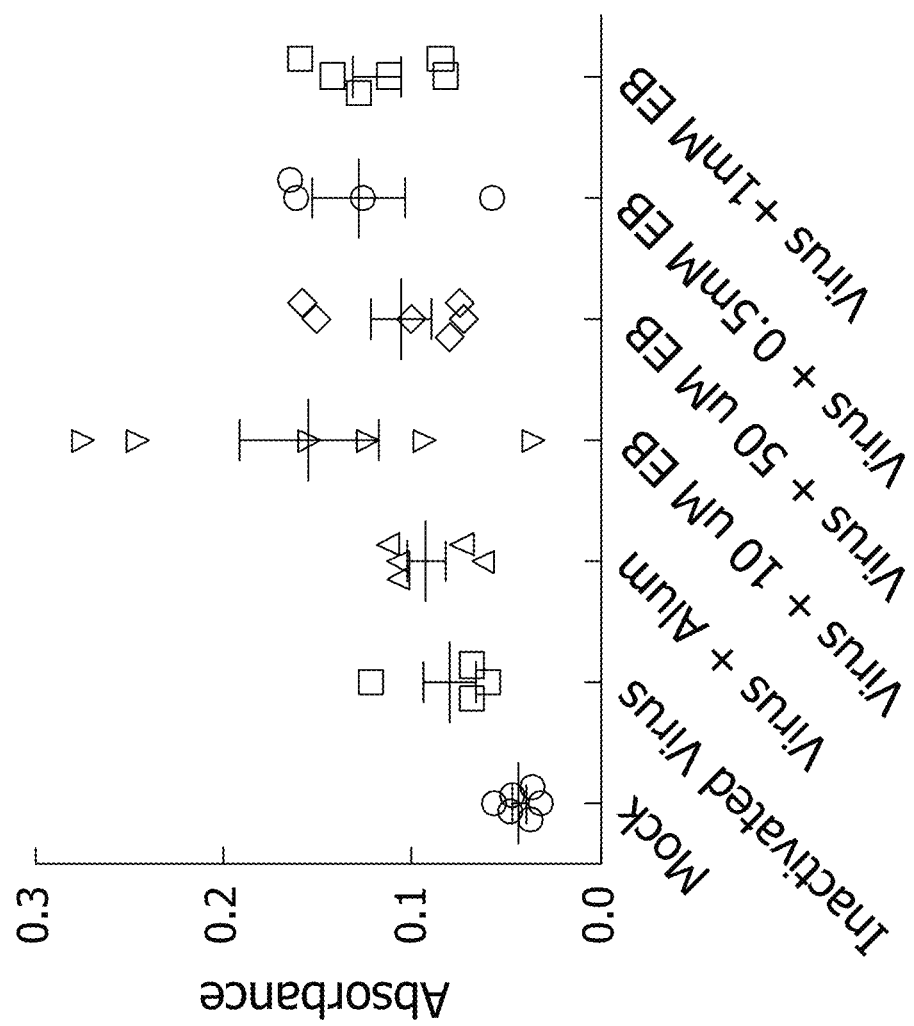
FIG. 4 is a chart depicting the results of influenza-specific IgG titers performed on blood obtained from mice 28 days post vaccination with either PBS (mock), inactivated VN/1203 virus alone, inactivated VN/1203 virus and alum, inactivated VN/1203 virus pretreated with 10 μM EB peptide, inactivated VN/1203 virus pretreated with 50 μM EB peptide, inactivated VN/1203 virus pretreated with 0.5 mM EB peptide, or inactivated VN/1203 virus pretreated with 1 mM EB peptide, as described in Example 3.

The results for titers at 28 days post-vaccination are shown in FIG. 4. Mice vaccinated with inactivated virus pretreated with EB peptide at all concentrations displayed increased virus specific IgG titers, as compared to mice vaccinated with non-adjuvanated vaccine (i.e., inactivated virus alone) or mice vaccinated with alum adjuvanated vaccine. A statistically significant difference was found between virus specific IgG titers for mock vaccinated mice and virus specific IgG titers for all vaccinated groups. There was no statistically significant difference in virus specific IgG titers for mice vaccinated with inactivated virus alone, mice vaccinated with inactivated virus plus alum, and mice vaccinated with inactivated virus and either 10 µM EB, 50 µM EB, 0.5 mM EB, or 1 mM EB. These results indicated that vaccination of mice with VN/1203 plus either 10 µM, 50 µM, 0.5 mM, or 1 mM EB resulted in increased virus specific IgG titers as compared to mice vaccinated with inactivated VN/1203 alone or mice vaccinated with inactivated VN/1203 plus alum.

Challenge: On day 29 post-initial vaccination, the mice were lightly anesthetized with isoflurane and intransally (i.n.) inoculated with VN/1203 (1 $MLD_{50}$). A group of mice (n=6) that had been vaccinated with inactivated VN/1203 and 200 µM EB, as previously described, was also inoculated. A control group of mice (n=6) that had been mock vaccinated, as previously described, was mock inoculated with 25 µL PBS.

The mice were monitored for weight loss for 12 days and clinical signs of infection for 10 days. A rating of 0=no signs of infection, 1=ruffled coat, hunched posture, 2=slowed movement, shivering, 3=labored breathing, anorexia, little to no movement, and 4=moribund. The results are shown in FIGS. 5 and 6.

Figure 5:
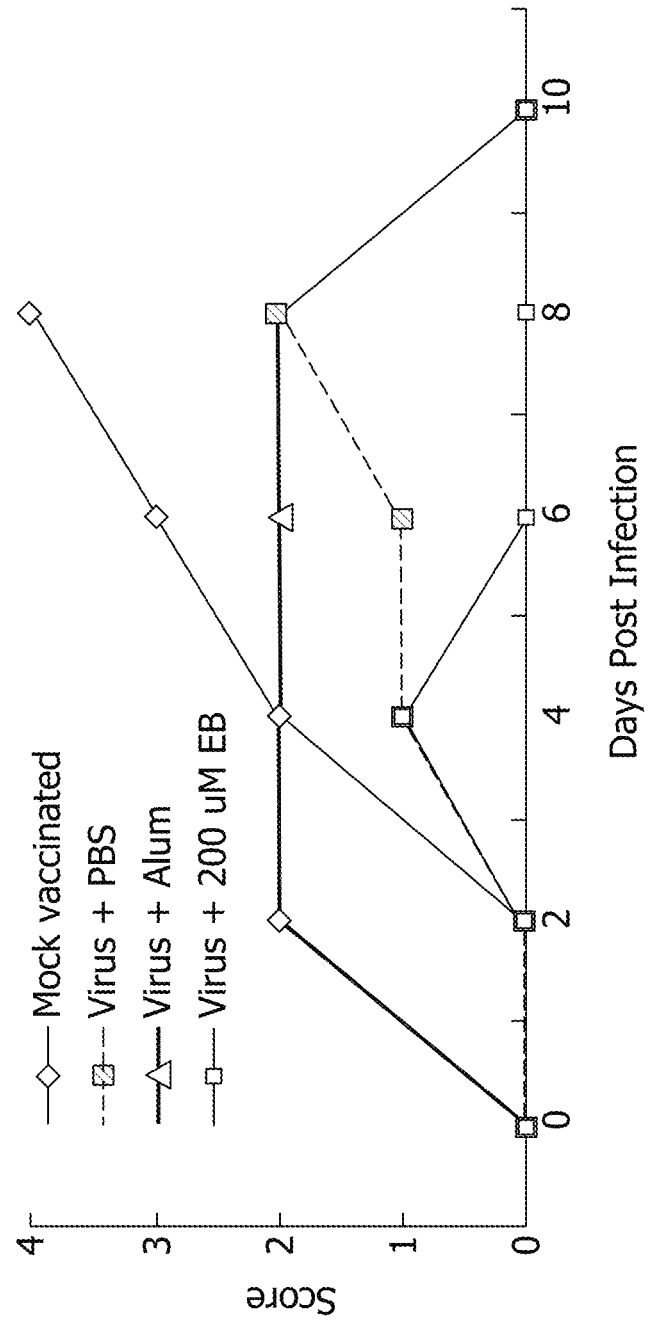
FIG. 5 is a chart depicting scores for clinical signs of infection at days 0-10 post-challenge for mice either mock vaccinated, vaccinated with inactivated virus plus PBS, vaccinated with inactivated virus plus alum, or vaccinated with inactivated virus plus EB, as described in Example 3.

As can be seen from FIG. 5, mice mock vaccinated were moribund by 8 days post infection. Mice vaccinated with inactivated VN/1203 plus PBS or with inactivated VN/1203 and alum showed signs of infection as late as day 8 post challenge (score of 2). In contrast, mice vaccinated with inactivated VN/1203 and 200 µM of EB had a score of 0 or 1 for all days post-challenge, indicating that vaccines comprising inactivated virus and EB are more effective at reducing clinical signs of infection than vaccine containing inactivated virus plus PBS or vaccine containing inactivated virus and alum.

Figure 6:
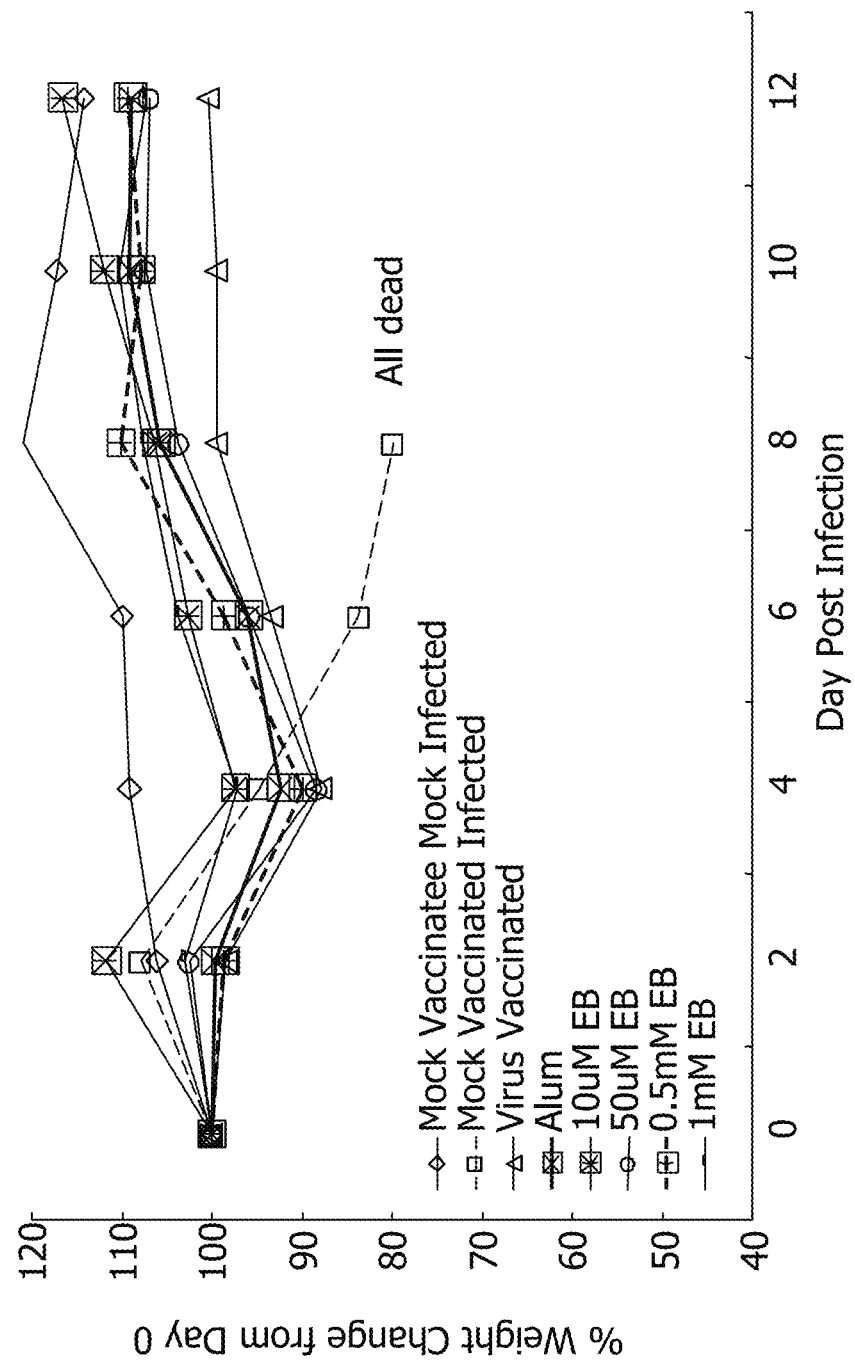
FIG. 6 is a chart depicting the percent weight change from day 0 of mice mock vaccinated (PBS), vaccinated with inactivated VN/1203 virus alone, vaccinated with inactivated VN/1203 and alum, or vaccinated with inactivated VN/1203 pretreated with 10 μM EB peptide, 50 μM EB peptide, 0.5 mM EB peptide, or 1 mM EB peptide 2 to 12 days post challenge with VN/1203 virus, as described in Example 3. A control group of mice mock vaccinated and mock infected with PBS was also tested.

As can be seen from FIG. 6, all mice mock vaccinated and infected with VN/1203 were dead by day 8 post infection. Mice vaccinated with inactivated VN/1203 plus PBS showed a slight decrease in weight at day 12 post-challenge. In contrast, mice vaccinated with inactivated VN/1203 and either alum or 10 µM, 50 µM, 0.5 mM or 1 mM of EB had a weight increase at 12 days post-challenge as compared to day 0 of challenge. Additionally, mice vaccinated with inactivated VN/1203 pretreated with either alum or 10 µM, 50 µM, 0.5 mM or 1 mM of EB weighed the same as or more than mice vaccinated with VN/1203 plus PBS at all days tested. These results indicate that vaccination of mice with inactivated VN/1203 pretreated with 10 µM to 1 mM of EB peptide does not result in significant weight loss, and has less of a negative impact on weight than does vaccination with VN/1203 plus PBS.

Lung Viral Titers: At day 7 post-challenge, 3 mice from each group were deeply anesthetized by isoflurane, sacrificed by cervical dislocation, and the lungs were extracted. This process was repeated for all remaining mice at day 10 post challenge. Tissues were homogenized in 1 ml of cold PBS containing antibiotics and viral titers in the lungs were determined by $TCID_{50}$ analysis on MDCK cells, as previously described. The results are shown in FIG. 7.

Figure 7:
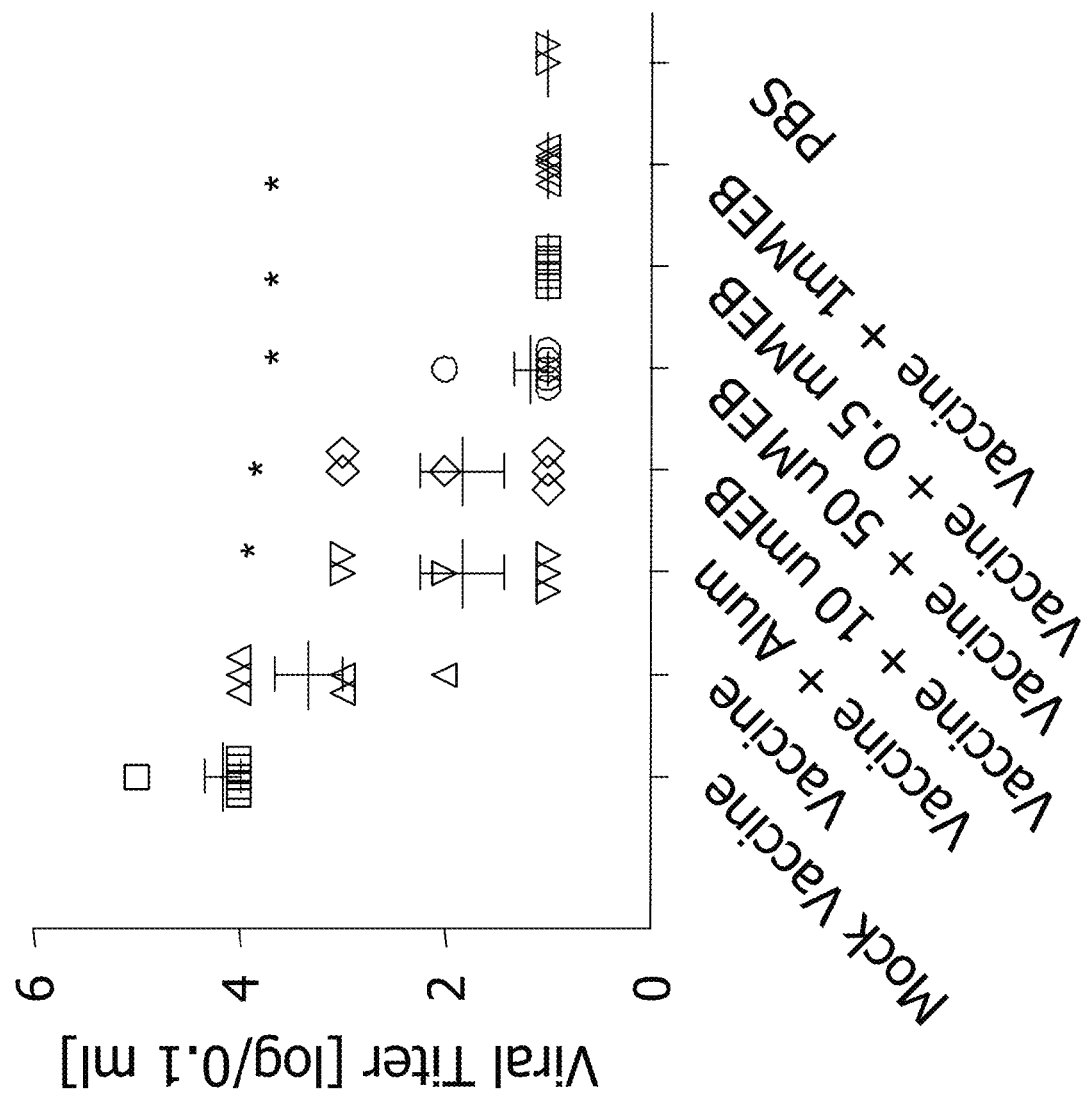
FIG. 7 is a chart depicting the results of lung viral titers from mice mock vaccinated (PBS), vaccinated with inactivated VN/1203 virus alone, vaccinated with inactivated VN/1203 and alum, or vaccinated with inactivated VN/1203 pretreated with 10 μM EB peptide, 50 μM EB peptide, 0.5 mM EB peptide, or 1 mM EB peptide 7 days post challenge with VN/1203 virus, as described in Example 3. A control group of mice mock vaccinated and mock infected with PBS was also tested. (*) represents statistical significance.

As can be seen from FIG. 7, mice vaccinated with VN/1203 pretreated with 50 µM or greater amounts of EB had no detectable infectious virus in their lungs at day 7 post-infection. In contrast, for mock vaccinated mice, mice vaccinated with inactivated VN/1203 plus PBS, and mice vaccinated with VN/1203 and alum, infectious virus was detected in the lungs, and in the case of the mock vaccinated mice, viral titers reached up to $10^4$ infectious viral particles in the lungs. These results suggest that avian influenza vaccine adjuvanated with the EB peptide may lead to a sterilizing immunity by inducing a stronger immune response than traditional influenza vaccine. There was no detectable infectious virus in the lungs of any of the groups vaccinated with inactivated VN/1203 and EB at day 10 (not shown).

Example 4

In this example, the ability of the EB peptide and a derivative thereof to enhance immunogenicity of an avian influenza vaccine composition comprising a suboptimal dose of antigen was evaluated in vivo.

To begin, vaccine compositions were prepared. A suboptimal dose of formalin-inactivated VN/1203 H5N1 virus (1 µg total protein, as determined by BCA assay, commercially available from Pierce Biotechnology) was incubated alone, with 0.5 mg/ml aluminum ammonium sulfate (alum), with 50

μM or 200 μM of the EB peptide (SEQ ID NO: 1), or with 200 μM of a derivative of the EB peptide having the sequence RRKKLPAVLLALLAP (SEQ ID NO: 4), for 1 hour at 37° C. All vaccines were prepared in sterile PBS. The SEQ ID NO: 4 peptide was prepared by retaining the RRKK (SEQ ID NO: 3) solubility tag and removing 5 amino acid residues from the N-terminus of the EB peptide.

Four to six weeks of age female Balb/C mice (n=10 per group) were injected with 50 μL of vaccine preparation or mock vaccinated with 50 μL PBS via intramuscular (i.m.) injection in the hind limb on day 0. Mice received a boost of vaccine or PBS (no boost) at day 15.

At 29 days post-initial vaccination (14 days after boost), the mice were lightly anesthetized with isoflurane and intranasally (i.n.) inoculated with VN/1203 (10 MLD$_{50}$). The mice were monitored for survival for 10 days and for weight loss and clinical signs of infection for 7 days. A rating of 0=no signs of infection, 1=slightly ruffled coat, shivering, 2=ruffled coat, labored breathing, 3=a ruffled coat, shallow breathing, shaking, anorexia. The results are shown in FIGS. 8-10.

Figure 8:
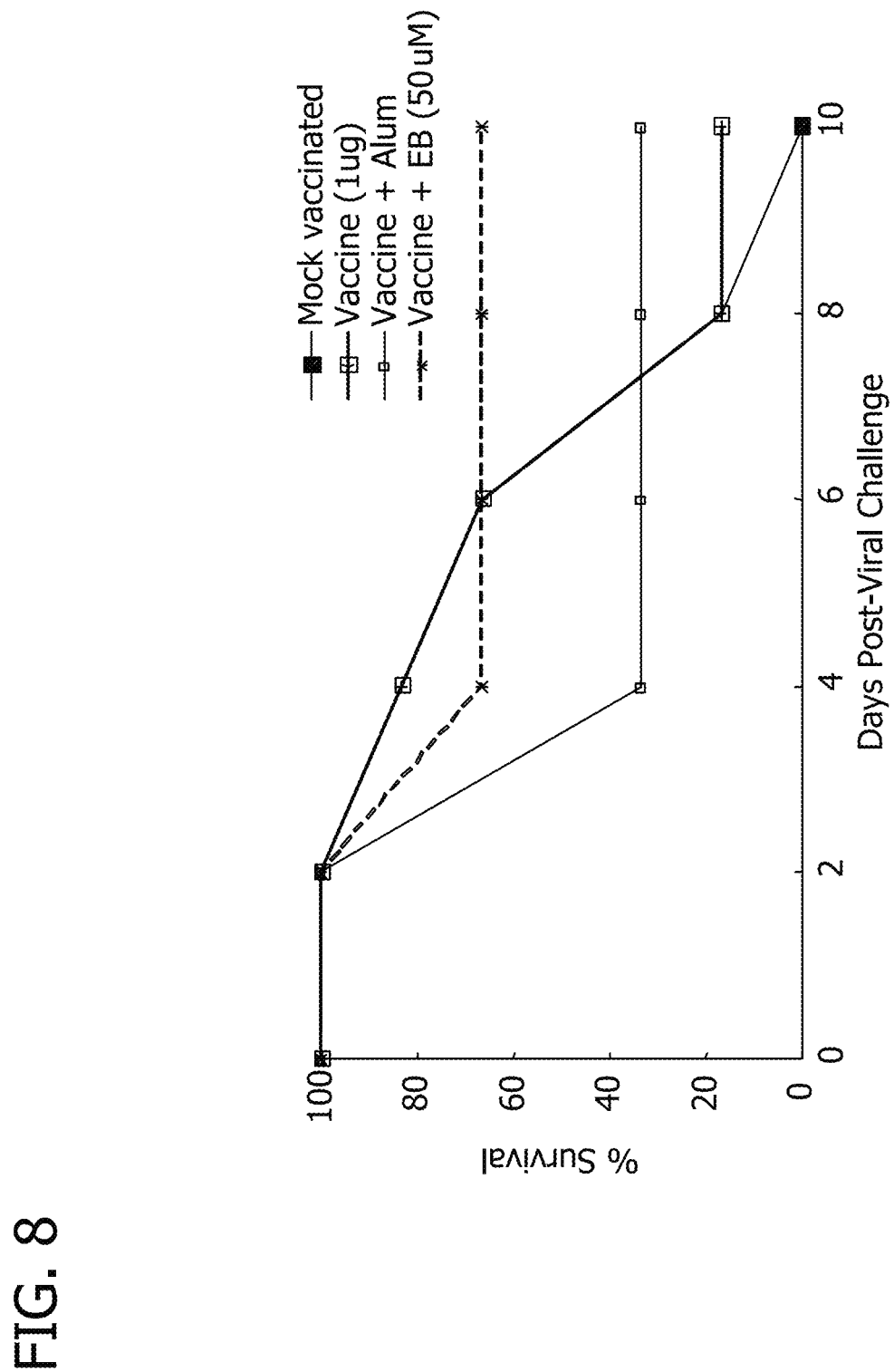
FIG. 8 is a chart depicting the percent survival of mice mock vaccinated (PBS), vaccinated with a suboptimal dose of inactivated VN/1203 virus alone, vaccinated with a suboptimal dose of inactivated VN/1203 virus plus alum, or vaccinated with a suboptimal dose of inactivated VN/1203 virus pretreated with 50 μM EB peptide, at days 0-10 post-challenge with VN/1203 virus, as discussed in Example 4.

As can be seen from FIG. 8, mice mock vaccinated with PBS were all dead by day 10 post-challenge, and mice vaccinated with a suboptimal dose of inactivated VN/1203 virus alone (i.e., no EB or alum) had a survival rate of less than 20%. In contrast, mice vaccinated with a suboptimal dose of inactivated VN/1203 virus pretreated with 50 μM of EB had a better than 60% rate of survival as late as 10 days post-viral challenge. These results indicate that EB increases the protection provided by avian influenza vaccines comprising a suboptimal dose of inactivated VN/1203 virus.

Figure 9:
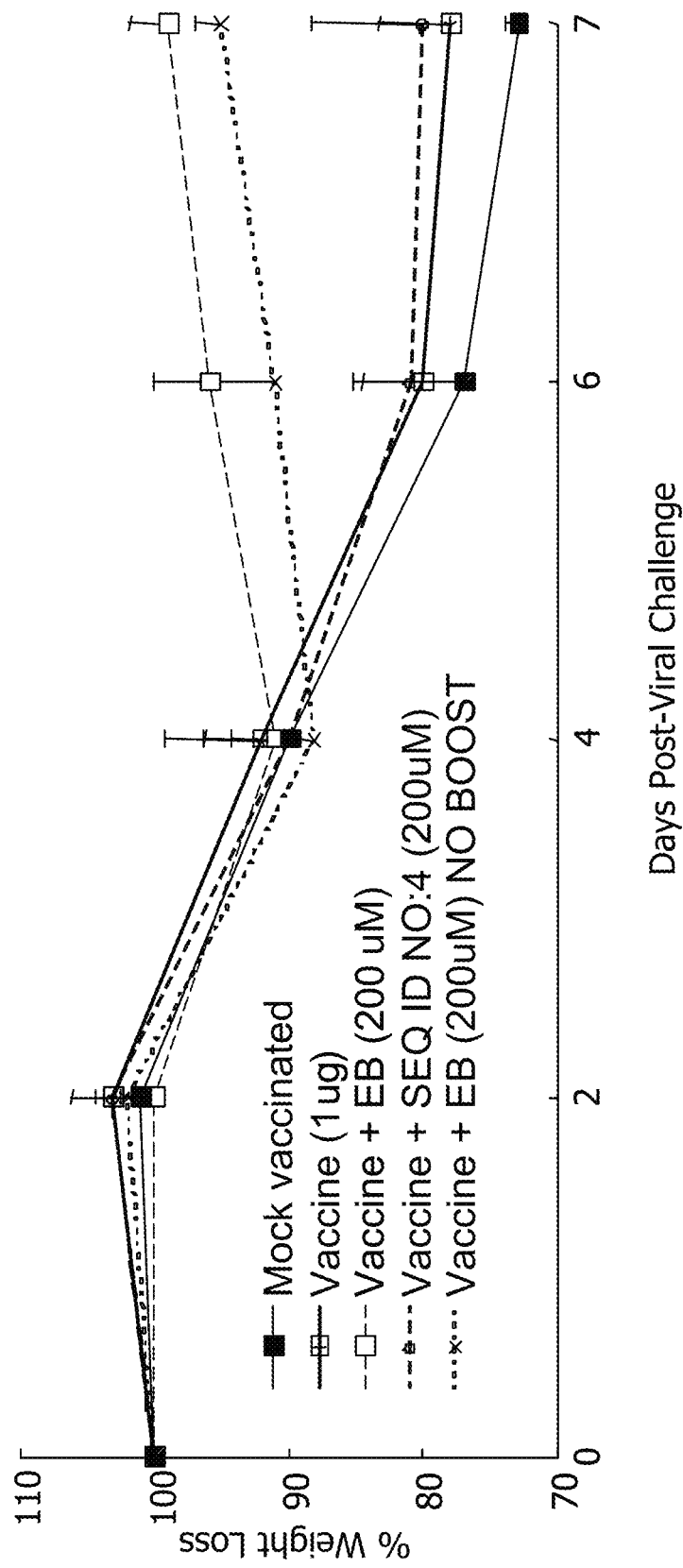
FIG. 9 is a chart depicting the percent weight loss of mice mock vaccinated (PBS), vaccinated with a suboptimal dose of inactivated VN/1203 virus alone, or vaccinated with a suboptimal dose of inactivated VN/1203 virus pretreated with 200 μM of the SEQ ID NO: 4 peptide, 200 μM EB peptide, or 200 μM EB peptide but not receiving a boost, 0-7 days post-challenge with VN/1203 virus, as discussed in Example 4.

As can be seen from FIG. 9, mice mock vaccinated with PBS and infected with VN/1203 virus experienced greater than 25% weight loss at day 7 post-challenge. Mice vaccinated with a suboptimal dose of inactivated VN/1203 virus alone and mice vaccinated with a suboptimal dose of inactivated VN/1203 virus pretreated with 200 μM of the SEQ ID NO: 4 peptide showed less weight loss at day 7 post viralchallenge than did mock vaccinated mice, but still exhibited around 20% weight loss. In contrast, mice vaccinated with a suboptimal dose of inactivated VN/1203 pretreated with 200 μM of the EB peptide showed little to no weight loss at day 7 post-viral challenge, even when the mice were not administered a boost of vaccine.

Figure 10:
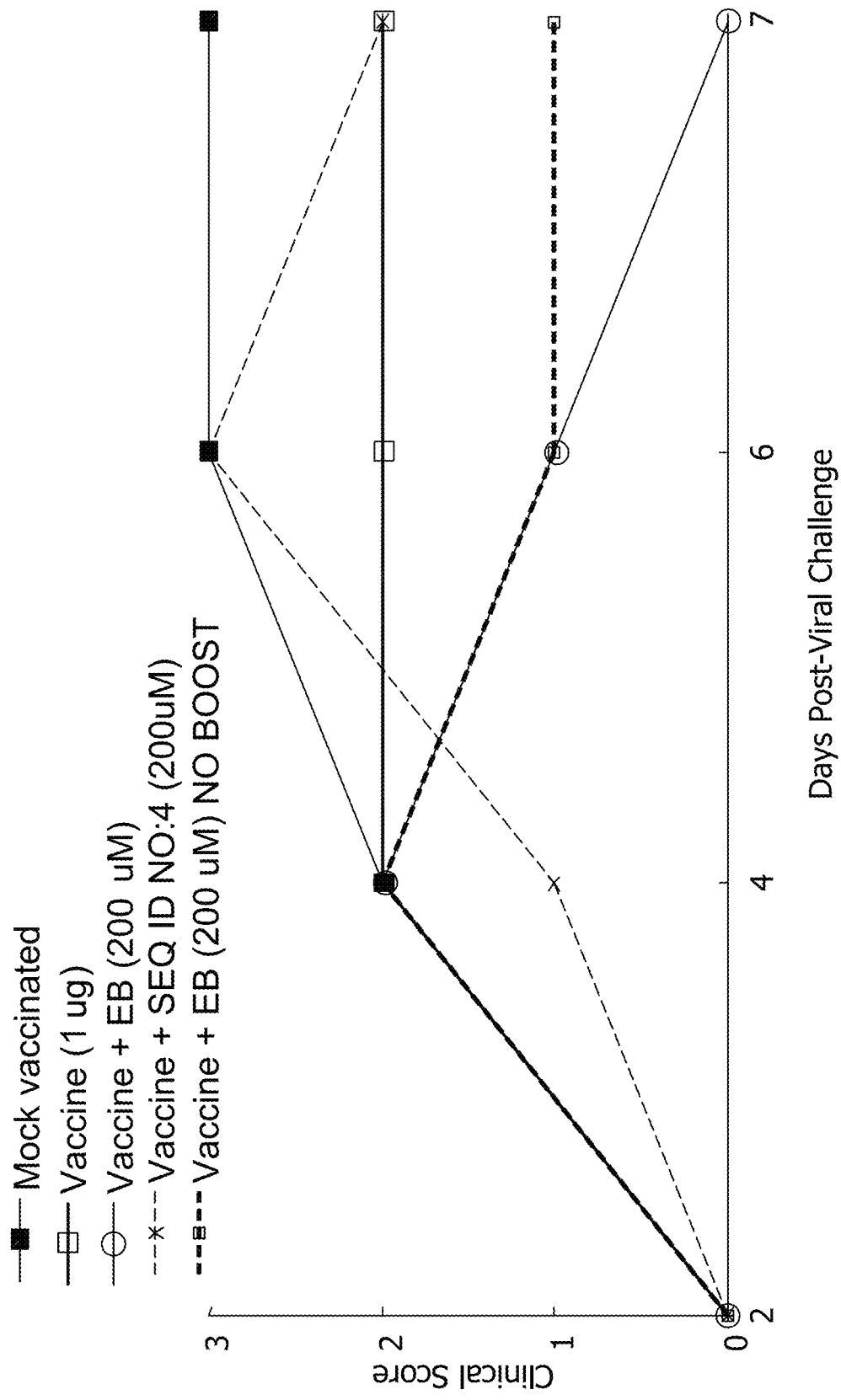
FIG. 10 is a chart depicting scores for clinical signs of infection at days 2-7 post-challenge for mice either mock vaccinated (PBS), vaccinated with a suboptimal dose of inactivated VN/1203 virus alone, or vaccinated with a suboptimal dose of inactivated VN/1203 virus pretreated with 200 μM of the SEQ ID NO: 4 peptide, 200 μM EB peptide, or 200 μM EB peptide but not receiving a boost, as discussed in Example 4.

As can be seen from FIG. 10, mice mock vaccinated and infected with VN/1203 virus showed significant signs of infection at day 7 post challenge (score of 3). Mice vaccinated with a suboptimal dose of inactivated VN/1203 alone and mice vaccinated with a suboptimal dose of inactivated VN/1203 pretreated with 200 μM of the SEQ ID NO: 4 peptide showed signs of infection as late as day 7 post-challenge (score of 2). In contrast, mice vaccinated with a suboptimal dose of inactivated VN/1203 pretreated with 200 μM of the EB peptide, with or without administration of a boost of vaccine, showed few to no signs of infection (scores of 0 and 1, respectively) on day 7 post-challenge. These results indicate that avian influenza vaccines comprising 200 μM of EB, with or without administration of a boost of vaccine, are more effective at reducing clinical signs of infection than vaccine alone or vaccine plus the SEQ ID NO: 4 peptide, when the vaccine contains a suboptimal dose of inactivated virus.

Lung Viral Titers: At days 4 and 7 post-challenge, 3 mice from each group were deeply anesthetized by isoflurane, sacrificed by cervical dislocation, and the lungs were extracted. Tissues were homogenized in 1 mL of cold PBS containing antibiotics and viral titers in the lungs were determined by TCID$_{50}$ analysis on MDCK cells, as previously described. Tests were performed in triplicate on individual mice. The results are shown in FIG. 11.

Figure 11:
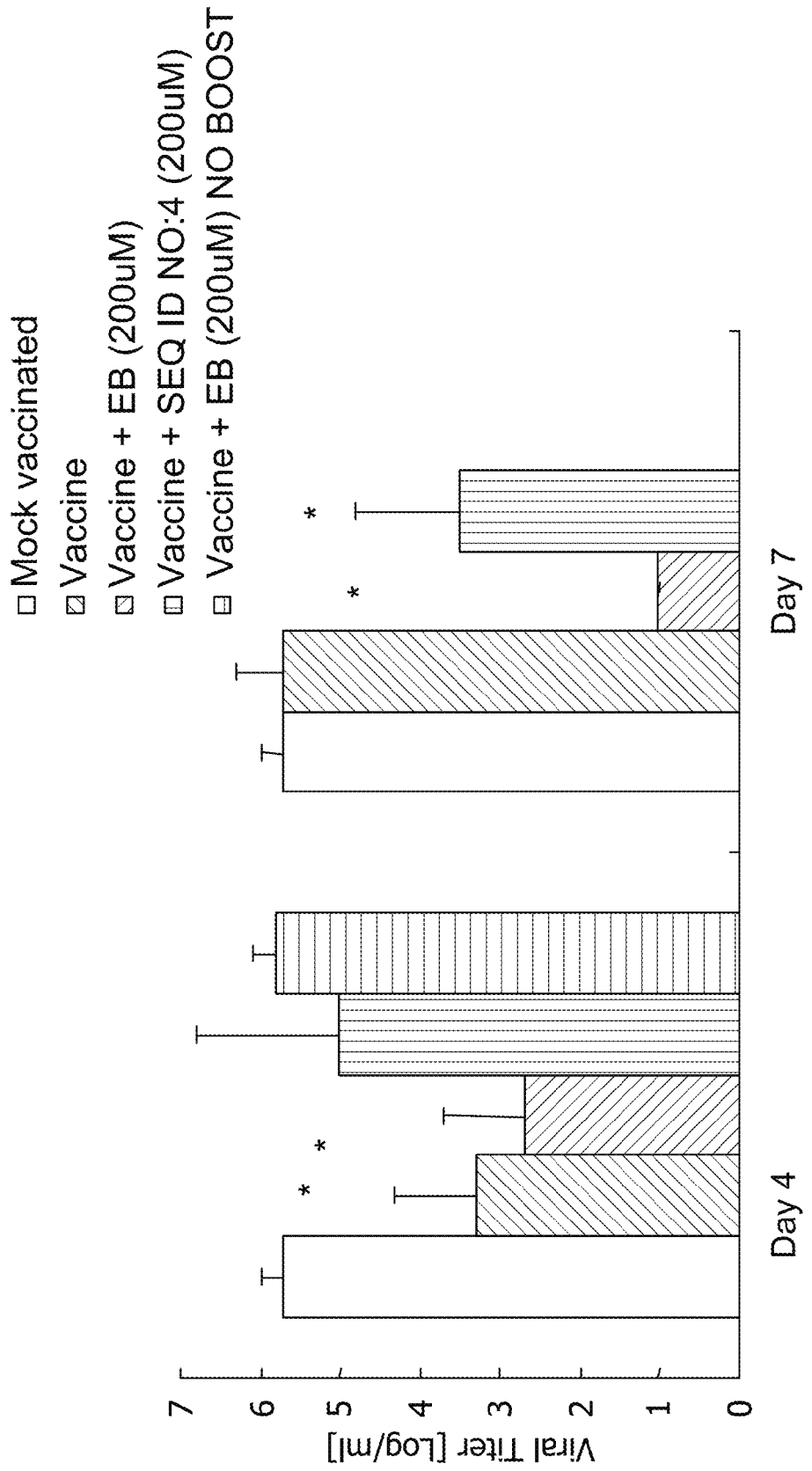
FIG. 11 is a chart depicting the results of lung viral titers from mice mock vaccinated (PBS), vaccinated with a suboptimal dose of inactivated VN/1203 virus alone, or vaccinated with a suboptimal dose of inactivated VN/1203 virus pretreated with 200 μM of the SEQ ID NO: 4 peptide, 200 μM EB peptide, or 200 μM EB peptide but not receiving a boost, at 4 and 7 days post challenge with VN/1203 virus, as discussed in Example 4. Error bars are standard deviation; (*) represents statistical significance.

As can be seen from FIG. 11, mice vaccinated with a suboptimal dose of VN/1203 pretreated with 200 μM of the SEQ ID NO: 4 peptide and mice vaccinated with a suboptimal dose of VN/1203 pretreated with 200 μM of the EB peptide, with or without administration of a boost of vaccine, had enhanced viral clearance at day 7 post-challenge as compared to mock vaccinated mice (PBS) and mice vaccinated with a suboptimal dose of VN/1203 alone. These results indicate that inclusion of 200 μM EB in an avian influenza vaccine containing a suboptimal dose of inactivated VN/1203 enhances viral clearance at day 7 post-challenge, without requiring the administration of a boost of vaccine.

Example 5

In this example, the ability of the EB peptide to enhance immunogenicity of an avian influenza vaccine composition by increasing total or serum-neutralizing antibodies was evaluated.

To begin, vaccine compositions were prepared. A suboptimal dose of formalin-inactivated VN/1203 H5N1 virus (1 μg total protein, as determined by BCA assay, commercially available from Pierce Biotechnology) was incubated alone, with 0.5 mg/ml aluminum ammonium sulfate (alum), or with 200 μM of the EB peptide (SEQ ID NO: 1) for 1 hour at 37° C. All vaccines were prepared in sterile PBS.

Four to six weeks of age female Balb/C mice (n=3 per group) were injected with 50 μL of vaccine preparation or mock vaccinated with 50 μL PBS (naive) via intramuscular (i.m.) injection in the hind limb on day 0. Blood was drawn from the tail vein prior to vaccination and at day 15 post-vaccination, and all mice received a boost of vaccine or PBS (mock vaccinated) at day 15. Mice were again bled at day 28 post initial vaccination. At 29 days post-initial vaccination, mice were intranasally challenged with VN/1203 virus (10 MLD$_{50}$), as described in Example 4. The mice were bled again and sera was collected on days 7 and 10 post-challenge.

Influenza-specific total IgG, IgG1, and IgG2 levels were determined by ELISA from day 28 post-initial vaccination serum (i.e., pre-challenge serum), using the procedure described in the Test Methods. Tests were performed in triplicate on individual mice and are representative of at least two separate experiments. The results are shown in FIG. 12.

Figure 12:
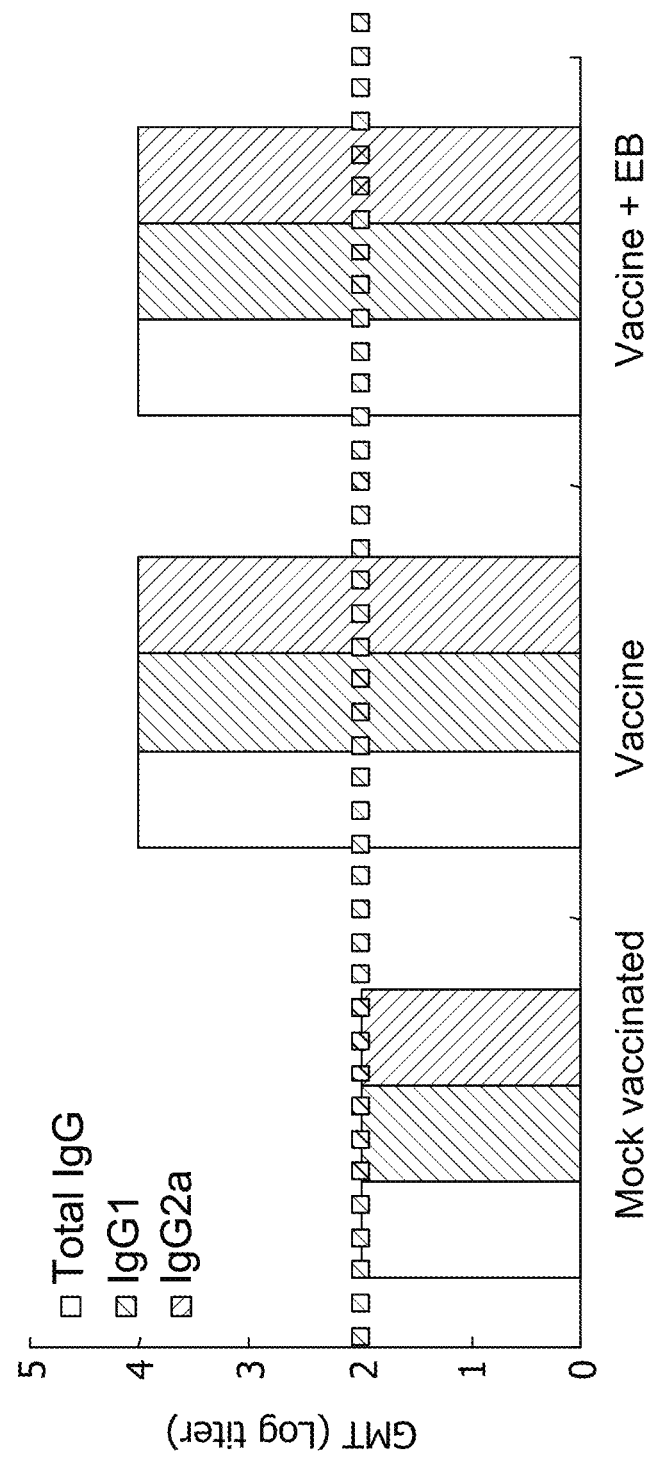
FIG. 12 is a graph depicting the results of influenza-specific total IgG, IgG1, and IgG2 titers performed on blood obtained from mice 28 days post vaccination with either PBS (mock vaccinated), a suboptimal dose of inactivated VN/1203 virus alone, or a suboptimal dose of inactivated VN/1203 virus pretreated with 200 μM EB peptide, as discussed in Example 5.

As can be seen from FIG. 12, the total IgG, IgG1, and IgG2 levels were the same for mice vaccinated with a suboptimal dose of VN/1203 alone and for mice vaccinated with a suboptimal dose of VN/1203 pretreated with 200 μM of EB peptide, suggesting that EB does not improve protection against avian influenza by increasing total antibodies.

The pre-vaccination serum and the day 15 and day 28 post-vaccination serum (i.e., pre-challenge serum) and the day 7 and day 10 post-challenge serum were analyzed for the presence of virus neutralizing antibodies using a microneutralization assay, as described in the Test Methods. Goat anti-H5N9 influenza virus sera (available from BEI Resources, Manassas, Va.) was used as a positive control. Tests were performed in triplicate on individual mice and are representative of at least two separate experiments. The results are shown in FIG. 13. As can be seen from FIG. 13, titers were negative for all sera, indicating that EB does not improve protection against avian influenza by increasing serum-neutralizing antibodies.

Example 6

In this example, the ability of the EB peptide to enhance immunogenicity of a seasonal influenza vaccine composition for a seasonal flu virus (a H1N1 virus) by increasing serum-neutralizing antibodies was evaluated.

To begin, vaccine compositions were prepared. A suboptimal dose of formalin-inactivated PR/8 H1N1 virus (1 µg total protein, as determined by BCA assay, commercially available from Pierce Biotechnology) was incubated alone, with 0.5 mg/ml aluminum ammonium sulfate (alum), with either 50 µM or 200 µM of the EB peptide (SEQ ID NO: 1), or with 50 µM or 200 µM of EBX, a 20-amino acid control peptide in which the amino acids making up the EB peptide sequence were scrambled, for 1 hour at 37° C. All vaccines were prepared in sterile PBS. EBX had the following sequence: RRKKLAALPLVLAAPLAVLA (SEQ ID NO: 5).

Four to six weeks of age female Balb/C mice (n=3 per group) were injected with 50 µL of vaccine preparation or mock vaccinated with 50 µL PBS via intramuscular (i.m.) injection in the hind limb on day 0. Blood was drawn from the tail vein and all mice received a boost of vaccine or PBS (mock vaccinated) at day 15. Mice were again bled at day 28 post initial vaccination. At 29 days post-initial vaccination, mice were intranasally challenged with PR/8 virus (10 $MLD_{50}$), as described in Example 4. The mice were monitored for survival for 6 days. The results are shown in FIG. 14A.

Figure 14A:
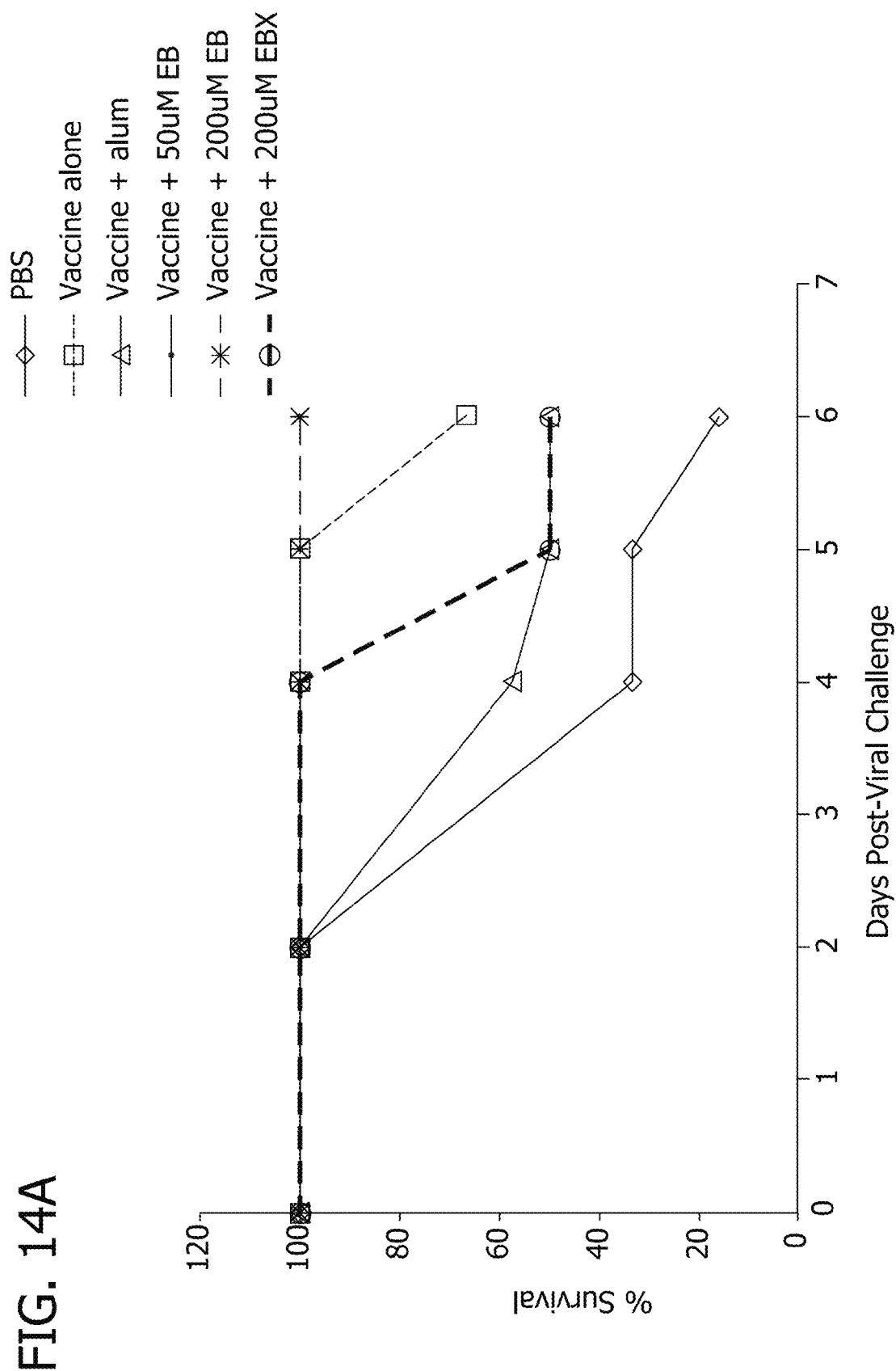
FIG. 14A is a chart depicting the percent survival of mice mock vaccinated (PBS), vaccinated with a suboptimal dose of inactivated PR/8 virus alone, vaccinated with a suboptimal dose of inactivated PR/8 virus plus alum, or vaccinated with a suboptimal dose of inactivated PR/8 virus pretreated with either 50 µM or 200 µM of EB peptide or 200 µM of EBX peptide, at days 0-6 post-challenge with PR/8 virus, as discussed in Example 6.

As can be seen from FIG. 14A, mice mock vaccinated with PBS had a survival rate of less than 40% at day 4 post-challenge, and less than 20% at day 6 post-challenge. Mice vaccinated with a suboptimal dose of inactivated PR/8 virus pretreated with either alum or 200µM of the EBX peptide had a survival rate of less than 60% at day 5 post-challenge, and mice vaccinated with a suboptimal dose of inactivated PR/8 virus alone (i.e., no EB or alum) had a survival rate of a little over 60% at day 6 post-challenge. In contrast, mice vaccinated with a suboptimal dose of inactivated PR/8 virus pretreated with 50 µM or 200 µM of EB had a 100% survival rate at day 6 post-challenge. These results indicate that EB increases the protection provided by seasonal influenza vaccines comprising a suboptimal dose of inactivated PR/8 virus.

Influenza-specific neutralizing antibodies were determined by hemagglutination inhibition assay, as described in the Test Methods. Values <40 are considered negative. Tests were performed in triplicate on pooled serum and are representative of at least two separate experiments. The results are shown in FIG. 14B.

As can be seen from FIG. 14B, titers were negative for all treatments at day 15 post-vaccination, suggesting that EB does not improve protection against seasonal influenza by increasing serum-neutralizing antibodies.

Example 7

In this example, the ability of EB to increase IFN-γ levels in mice vaccinated with inactivated avian influenza virus was evaluated.

To begin, vaccine compositions were prepared. A suboptimal dose of formalin-inactivated VN/1203 H5N1 virus (1 µg total protein, as determined by BCA assay, commercially available from Pierce Biotechnology) was incubated alone or with 200 µM of the EB peptide (SEQ ID NO: 1) for 1 hour at 37° C. All vaccines were prepared in sterile PBS.

Four to six weeks of age female Balb/C mice (n=2 per group) were injected with 50 µL of vaccine preparation or mock vaccinated with 50 µL PBS via intramuscular (i.m.) injection in the hind limb on day 0. All mice received a boost of vaccine or PBS (mock vaccinated) at day 15. Splenocytes were isolated from the mice at 15 and 28 days post vaccination, using the procedure described above. Isolated splenocytes were stimulated with R10 media alone or R10 media containing 1 µg/mL formalin inactivated VN/1203 virus and IFN-γ secreting splenocytes were determined by ELISpot assay, using the procedure described in the Test Methods. CD3 antibody was used as a positive control and yielded >100 spots (data not shown). Data are presented as the mean values±standard errors of the mean. The results are shown in FIG. 15.

Figure 15:
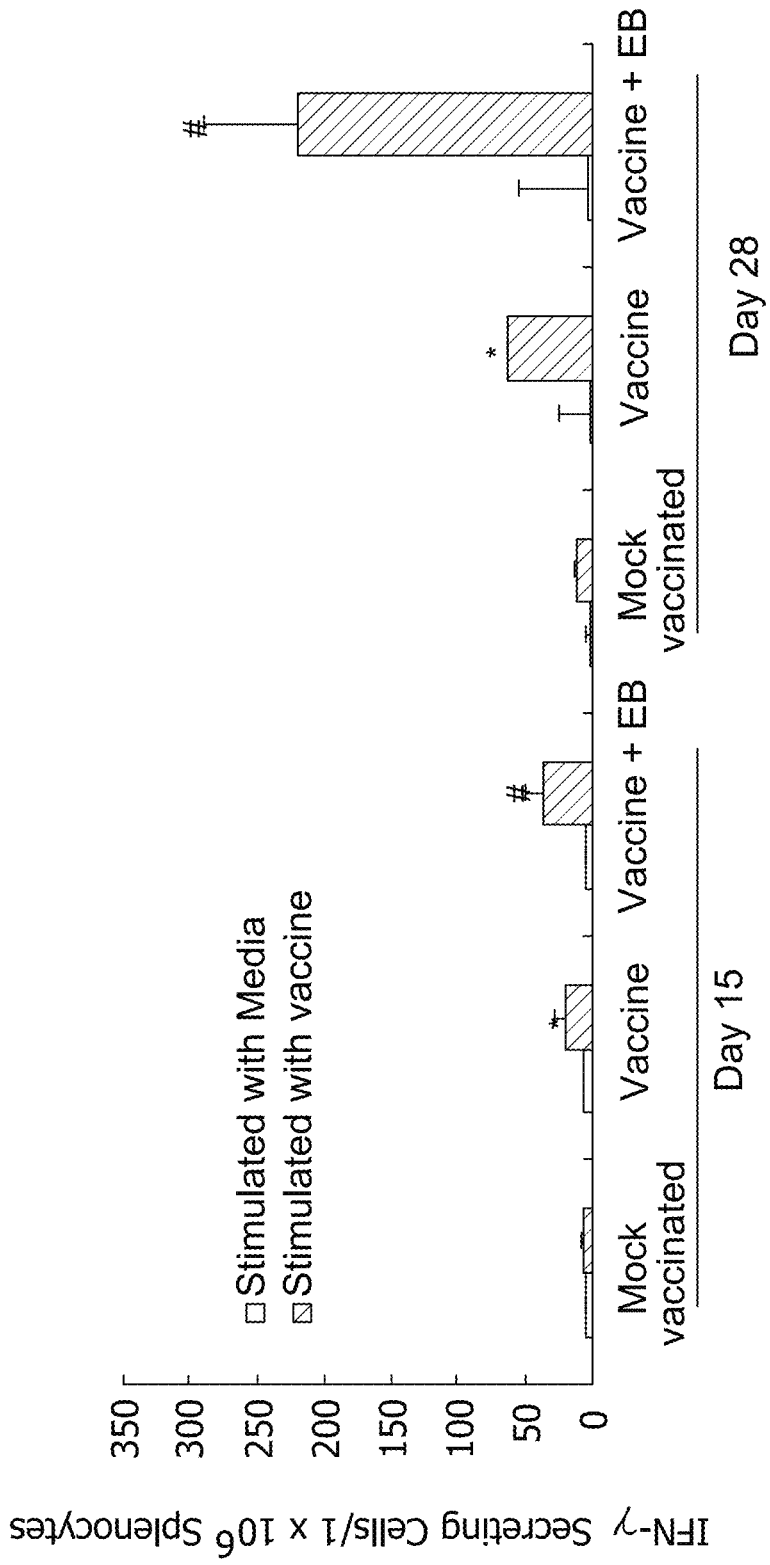
FIG. 15 is a chart depicting IFN-γ levels in mice mock vaccinated, vaccinated with inactivated VN/1203 virus alone, or vaccinated with inactivated VN/1203 virus pretreated with 200 µM of the EB peptide, at day 15 and day 28 post-vaccination, as discussed in Example 7.

As can be seen from FIG. 15, the EB peptide increases IFN-γ levels in mice vaccinated with inactivated VN/1203 virus, suggesting that T cells are stimulated. Stimulation of cellular immunity is not seen with vaccines comprising inactivated VN/1203 virus alone.

Example 8

In this example, the ability of EB to increase IFN-γ levels in mice vaccinated with an inactivated seasonal influenza virus was evaluated.

To begin, vaccine compositions were prepared. A suboptimal dose of formalin-inactivated PR/8 H1N1 virus (1 µg total protein, as determined by BCA assay, commercially available from Pierce Biotechnology) was incubated alone or with either 50 µM or 200 µM of the EB peptide (SEQ ID NO: 1) or with 200 µM of the EBX peptide (SEQ ID NO: 5) for 1 hour at 37° C. All vaccines were prepared in sterile PBS.

Four to six weeks of age female Balb/C mice (n=3 per group) were injected with 50 µL of vaccine preparation, injected 50 µL of either 200 µM of the EB or 200 µM of the EBX peptide, or mock vaccinated with 50 µL PBS via intramuscular (i.m.) injection in the hind limb on day 0. All mice received a boost of vaccine or PBS (mock vaccinated) at day 15. Splenocytes were isolated from the mice at 15 days post vaccination, using the procedure described above. Isolated splenocytes were stimulated with R10 media alone or R10 media containing concavalin A (1 µg/mL), formalin inactivated PR/8 virus (1 µg), or inactivated VN/1203 virus (1 µg). IFN-γ secreting splenocytes were determined by ELISpot assay, using the procedure described in the Test Methods. Data are presented as the mean values±standard errors of the mean relative to concavalin A stimulated splenocytes. The results are shown in FIG. 16.

Figure 16:
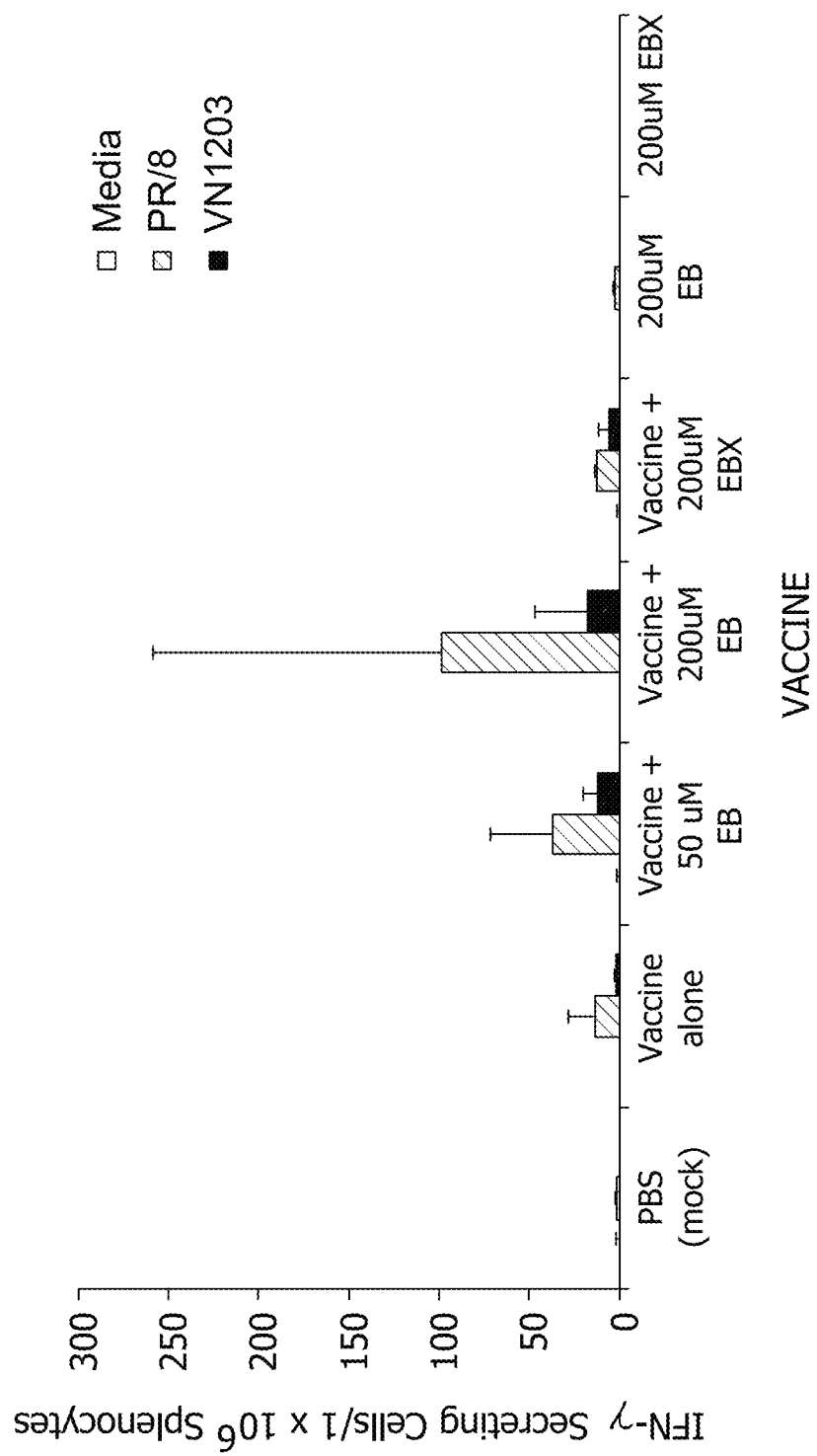
FIG. 16 is a chart depicting IFN-γ levels in mice mock vaccinated (PBS), vaccinated with inactivated PR/8 virus alone, vaccinated with inactivated PR/8 virus pretreated with either 50 µM or 200 µM EB peptide or 200 µM EBX peptide, or injected with either 200 µM EB peptide or 200 µM EBX peptide, at day 15 post-vaccination, as discussed in Example 8.

As can be seen from FIG. 16, the EB peptide increases IFN-γ levels in mice vaccinated with inactivated PR/8 virus, suggesting that T cells are stimulated. Stimulation of cellular immunity is not seen with vaccines comprising inactivated PR/8 virus alone.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A vaccine comprising an immunogen and an adjuvant peptide having the formula:

$$(X1)_n\text{-A-A-V-A-L-L-P-A-V-L-L-A-L-L-A-P-}(x2)_m,$$
(SEQ ID NO: 2)

wherein X1 and X2 are selected from one or more charged amino acid residues, each X1 and each X2 may be the same or different charged amino acid residues, n is 0 or 3-10, and m is 0 or 3-10, but wherein m and n are not both 0; and wherein the immunogen is capable of eliciting an immune response against a respiratory virus.

2. The vaccine of claim 1 wherein the adjuvant peptide has the sequence RRKKAAVALLPAVLLALLAP (SEQ ID NO: 1).

3. The vaccine of claim 1, wherein the immunogen is an antigen.

4. The vaccine of claim 3 wherein the antigen is selected from the group consisting of a split virus antigen, a subunit antigen, an inactivated whole virus, a live attenuated virus, or combinations thereof.

5. The vaccine of claim 1 wherein the vaccine comprises the immunogen in an amount of from about 1 μg per mL to about 10 μg per mL.

6. The vaccine of claim 1 further comprising a pharmaceutically acceptable carrier.

7. The vaccine of claim 1 wherein the respiratory virus is an influenza virus.

8. The vaccine of claim 7 wherein the influenza virus is selected from the group consisting of an avian influenza virus and a seasonal influenza virus.

9. The vaccine of claim 8 wherein the avian influenza virus is H5N1.

10. The vaccine of claim 7 wherein the influenza virus is influenza A virus.

11. A method of immunizing a mammal against a viral respiratory infection, the method comprising administering to the mammal a vaccine comprising an immunogen and an adjuvant peptide having the formula:

$$(X1)_n\text{-A-A-V-A-L-L-P-A-V-L-L-A-L-L-A-P-}(x2)_m,$$
(SEQ ID NO: 2)

wherein X1 and X2 are selected from one or more charged amino acid residues, each X1 and each X2 may be the same or different charged amino acid residues, n is 0 or 3-10, and m is 0 or 3-10, but wherein m and n are not both 0; and wherein the immunogen is capable of eliciting an immune response against a respiratory virus.

12. The method of claim 11 wherein the adjuvant peptide has the sequence RRKKAAVALLPAVLLALLAP (SEQ ID NO: 1).

13. The method of claim 11, wherein the immunogen is an antigen.

14. The method of claim 13 wherein the antigen is selected from the group consisting of a split virus antigen, a subunit antigen, an inactivated whole virus, a live attenuated virus, or combinations thereof.

15. The method of claim 11 wherein the respiratory virus is an influenza virus.

16. The method of claim 15 wherein the influenza virus is an avian influenza virus.

17. The method of claim 15 wherein the respiratory virus is a seasonal influenza virus.

18. The method of claim 11 wherein the vaccine is administered through parenteral administration.

19. The method of claim 11 wherein the vaccine is administered intranasally.

20. The method of claim 11 wherein the vaccine is administered prophylactically.

* * * * *